(12) United States Patent
Yodfat et al.

(10) Patent No.: US 10,493,203 B2
(45) Date of Patent: Dec. 3, 2019

(54) DEVICES AND METHODS FOR POWERING A MEDICAL DEVICE

(71) Applicant: Roche Diabetes Care, Inc., Indianapolis, IN (US)

(72) Inventors: Ofer Yodfat, Maccabim-Reut (IL); Avihoo P. Keret, Kfar Vradim (IL)

(73) Assignee: Roche Diabetes Care, Inc., Indianapolis, IN (US)

( * ) Notice: Subject to any disclaimer, the term of this patent is extended or adjusted under 35 U.S.C. 154(b) by 0 days.

(21) Appl. No.: 15/435,861

(22) Filed: Feb. 17, 2017

(65) Prior Publication Data
US 2017/0157324 A1 Jun. 8, 2017

Related U.S. Application Data

(63) Continuation of application No. 13/958,255, filed on Aug. 2, 2013, now Pat. No. 9,572,924, which is a (Continued)

(51) Int. Cl.
*A61M 5/172* (2006.01)
*A61B 5/145* (2006.01)
(Continued)

(52) U.S. Cl.
CPC ........... *A61M 5/1723* (2013.01); *A61B 5/145* (2013.01); *A61B 5/14532* (2013.01);
(Continued)

(58) Field of Classification Search
CPC .... A61M 2005/14268; A61M 5/14212; A61M 5/14244; A61M 5/14232;
(Continued)

(56) References Cited

U.S. PATENT DOCUMENTS

| 3,631,847 A | 1/1972 | Hobbs |
| 3,771,694 A | 11/1973 | Kaminski |

(Continued)

FOREIGN PATENT DOCUMENTS

| WO | 2004032994 A2 | 4/2004 |
| WO | 2004032994 A3 | 6/2004 |

(Continued)

OTHER PUBLICATIONS

Boizel, R., "Glucose monitoring and pump data management software operated on a personal digital assistant can contribute to improve diabetes control in CSII-treated patients", Diabetes Metab. 33:314-315 (2007).

(Continued)

*Primary Examiner* — Quynh-Nhu H. Vu
(74) *Attorney, Agent, or Firm* — Dinsmore & Shohl, LLP

(57) ABSTRACT

Devices and methods for powering a medical device for sustained delivery of fluids or continuous monitoring of body analyte are disclosed. The devices may comprise a pumping mechanism, a driving mechanism for activating the pumping mechanism to dispense fluid, and a power source coupled to the driving mechanism and having an energy storage cell for providing a pulsed power to the driving mechanism. The methods may be implemented by activating the driving mechanism using pulsed energy in the form of at least one pulse train pattern accumulated in and discharged from an energy storage component.

16 Claims, 19 Drawing Sheets

Related U.S. Application Data continuation of application No. 12/809,223, filed as application No. PCT/IL2008/001650 on Dec. 21, 2008, now Pat. No. 8,500,692.

(60) Provisional application No. 61/065,142, filed on Feb. 8, 2008, provisional application No. 61/008,693, filed on Dec. 21, 2007.

(51) Int. Cl.
  *A61M 5/142* (2006.01)
  *A61B 5/00* (2006.01)
(52) U.S. Cl.
  CPC ....... *A61B 5/4839* (2013.01); *A61M 5/14212* (2013.01); *A61M 5/14244* (2013.01); *A61M 5/14248* (2013.01); *A61B 2560/0209* (2013.01); *A61B 2560/0214* (2013.01); *A61B 2560/0412* (2013.01); *A61B 2560/0443* (2013.01); *A61M 2005/14268* (2013.01)
(58) Field of Classification Search
  CPC .... A61B 2560/0209; A61B 2560/0214; A61B 2560/0412; A61B 2560/0443
  See application file for complete search history.

(56) References Cited

U.S. PATENT DOCUMENTS

| | | | |
|---|---|---|---|
| 3,865,988 A * | 2/1975 | Getgen | H04J 3/20 370/308 |
| 4,150,672 A | 4/1979 | Martin et al. | |
| 4,346,463 A * | 8/1982 | Tu Xuan | G04C 3/143 318/696 |
| 4,498,843 A | 2/1985 | Schneider et al. | |
| 4,544,369 A | 10/1985 | Skakoon et al. | |
| 4,552,513 A * | 11/1985 | Miller | F04B 11/0058 417/18 |
| 4,657,486 A | 4/1987 | Stempfle et al. | |
| 4,808,077 A * | 2/1989 | Kan | F04B 11/0058 417/18 |
| 4,810,168 A * | 3/1989 | Nogami | F04B 11/00 210/101 |
| 5,114,314 A * | 5/1992 | Fujimoto | F04B 11/0058 417/18 |
| 5,774,426 A * | 6/1998 | Tu | H02P 8/16 368/157 |
| 5,919,167 A | 7/1999 | Mulhauser et al. | |
| 5,938,640 A | 8/1999 | Maget et al. | |
| 5,949,632 A * | 9/1999 | Barreras, Sr. | H02M 3/156 361/90 |
| 5,957,895 A | 9/1999 | Sage et al. | |
| 6,056,716 A | 5/2000 | D Antonio et al. | |
| 6,462,507 B2 * | 10/2002 | Fisher, Jr. | H02J 7/0068 307/66 |
| 6,485,461 B1 | 11/2002 | Mason et al. | |
| 6,589,229 B1 | 7/2003 | Connelly et al. | |
| 6,723,072 B2 | 4/2004 | Flaherty et al. | |
| 6,740,059 B2 | 5/2004 | Flaherty | |
| 7,122,026 B2 | 10/2006 | Rogers et al. | |
| 7,144,384 B2 | 12/2006 | Gorman et al. | |
| 7,485,461 B2 | 2/2009 | Hammer | |
| 8,390,244 B2 * | 3/2013 | Wooley | A61M 5/14244 307/66 |
| 8,500,692 B2 * | 8/2013 | Yodfat | A61B 5/4839 604/131 |
| 9,572,924 B2 * | 2/2017 | Yodfat | A61B 5/4839 |
| 2002/0072733 A1 | 6/2002 | Flaherty | |
| 2003/0199855 A1 * | 10/2003 | Rogers | A61M 5/14276 604/891.1 |
| 2003/0229310 A1 | 12/2003 | Flaherty et al. | |
| 2004/0010207 A1 * | 1/2004 | Flaherty | A61B 5/14532 600/573 |
| 2004/0064088 A1 * | 4/2004 | Gorman | A61M 5/14276 604/93.01 |
| 2007/0073235 A1 | 3/2007 | Estes et al. | |
| 2007/0106218 A1 | 5/2007 | Yodfat et al. | |
| 2007/0159755 A1 * | 7/2007 | Talbot | A61M 5/142 361/115 |
| 2007/0191702 A1 * | 8/2007 | Yodfat | A61B 5/14525 600/365 |
| 2008/0097326 A1 * | 4/2008 | Moberg | A61M 5/1413 604/155 |
| 2008/0215035 A1 | 9/2008 | Yodfat et al. | |
| 2010/0191078 A1 | 7/2010 | Yodfat et al. | |

FOREIGN PATENT DOCUMENTS

| | | |
|---|---|---|
| WO | 2006102412 A2 | 9/2006 |
| WO | 2007052277 A1 | 5/2007 |
| WO | 2006102412 A3 | 11/2007 |
| WO | 2008078318 A2 | 7/2008 |
| WO | 2008078318 A3 | 9/2008 |
| WO | 2008139458 A2 | 11/2008 |
| WO | 2008139459 A1 | 11/2008 |
| WO | 2008139458 A3 | 3/2009 |
| WO | 2009125398 A2 | 10/2009 |
| WO | 2009125398 A3 | 2/2010 |

OTHER PUBLICATIONS

Hoogma et al., "Comparison of the effects of continuous subcutaneous insulin infusion (CSII) and NPH-based multiple daily insulin injections (MDI) on glycaemic control and quality of life: results of the 5-nations trial", Diabetes Med. 23(2):141-147 (2007).

International Search Report for PCT Application No. PCT/IL2008/001650, dated May 4, 2009.

Parkner et al., "Overnight CSII as supplement to oral antidiabetic drugs in Type 2 diabetes", Diabetes Obes. Metab., 10:556-563 (2007).

Written Opinion of the International Search Authority for PCT Application No. PCT/IL2008/001650, dated May 4, 2009.

Texas Instruments, "Single-Chip, Li-Ion Charge Management IC for Handheld Applications (bqTINY) Check for Samples: bq24010, bq24012, bq24013, bq24014, bq24018"; Sep. 2002-Revised Jan. 2014, Texas Instruments Incorporated, www.ti.com.

* cited by examiner

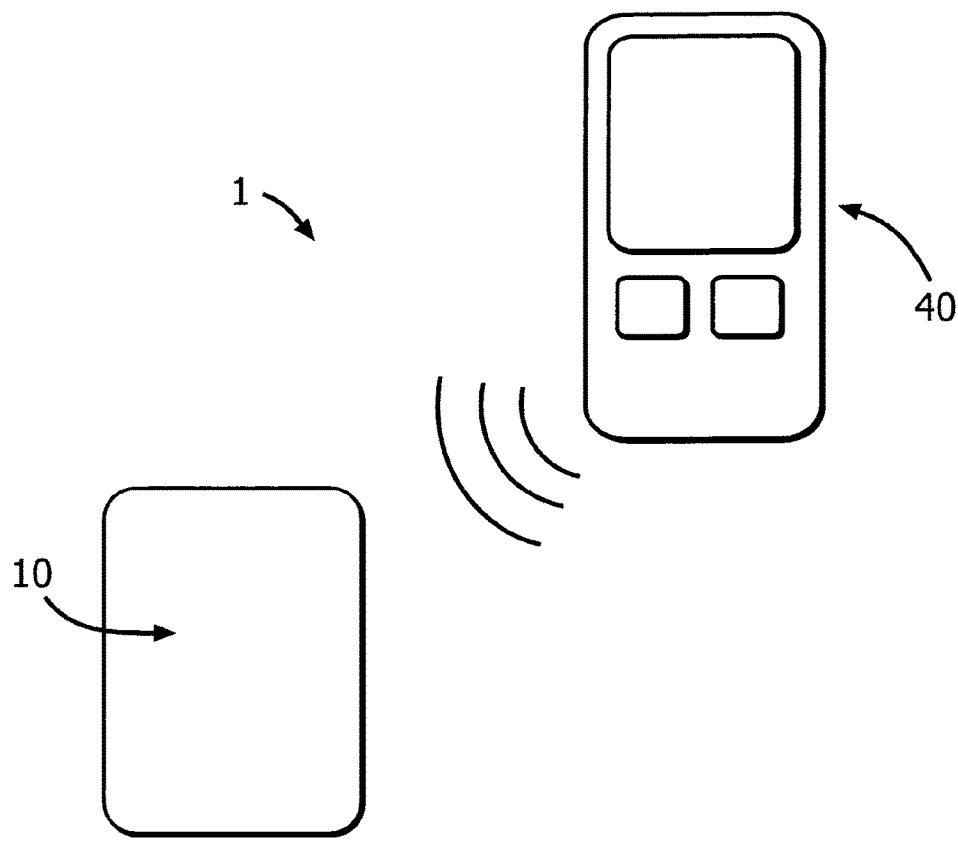
FIG. 1a
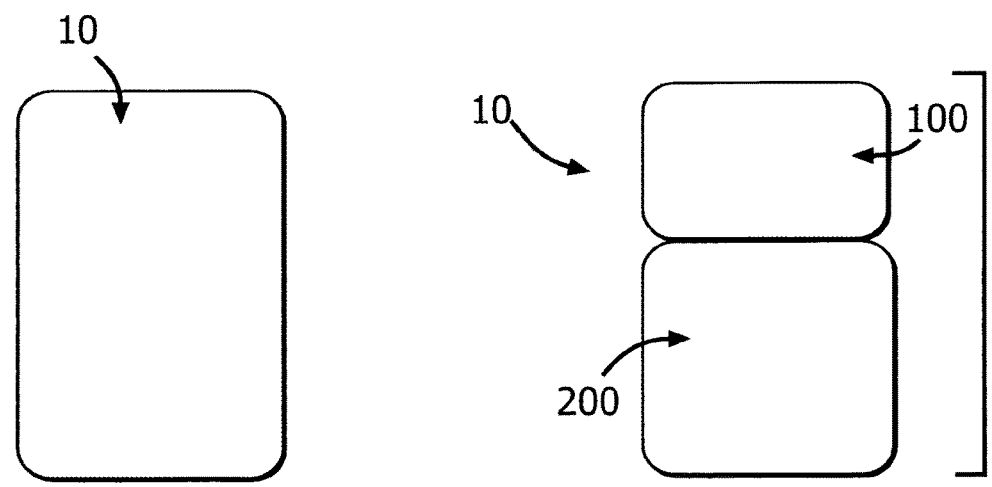
FIG. 1b  FIG. 1c

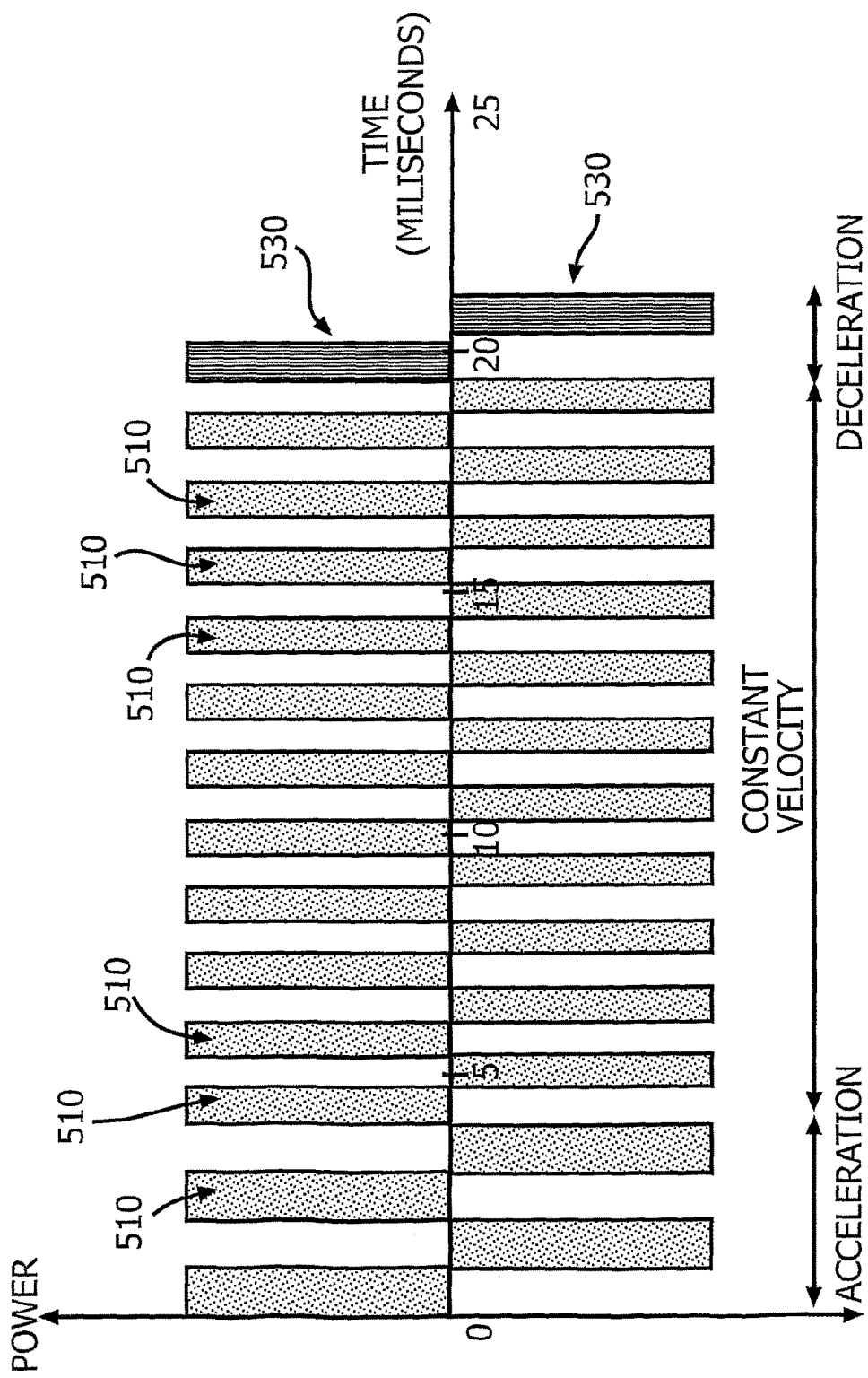

DEVICES AND METHODS FOR POWERING A MEDICAL DEVICE

CROSS-REFERENCE TO RELATED APPLICATIONS

The present application is a continuation of U.S. Non-Provisional application Ser. No. 13/958,255 filed Aug. 2, 2013, which is a continuation of U.S. Non-Provisional application Ser. No. 12/809,223, filed Jun. 18, 2010, now U.S. Pat. No. 8,500,692, which is a 35 U.S.C. § 371 national stage entry of PCT/IL2008/001650, which has an international filing date of Dec. 21, 2008 and claims priority to U.S. Provisional Patent Application No. 61/065,142, filed on Feb. 8, 2008 and U.S. Provisional Patent Application No. 61/008,693, filed on Dec. 21, 2007. The present application incorporates herein by reference the contents of each of the above-referenced applications in their entireties.

FIELD

Devices and methods for sustained delivery of fluids and/or continuous monitoring of body analyte are described herein. More particularly, a portable infusion, patch-like pump, adherable to the skin that can also continuously monitor body analytes is described. Also provided herein is a fluid dispensing and/or body analyte monitoring device having a power source and components for energy conservation.

BACKGROUND

Medical treatment of certain illnesses requires continuous drug infusion into various body compartments, such as subcutaneous and intravenous injections. Diabetes mellitus (DM) patients, for example, require the administration of varying amounts of insulin throughout the day to control their blood glucose levels. In recent years, ambulatory portable insulin infusion pumps have emerged as a superior alternative to multiple daily syringe injections of insulin for Type 1 (Diabetes Medicine 2006; 23(2):141-7) and Type 2 (Diabetes Metab 2007 Apr. 30, Diabetes Obes Metab 2007 Jun. 26) diabetes patients. These pumps, which deliver insulin at a continuous basal rate, as well as in bolus volumes, were developed to liberate patients from repeated self-administered injections and allow them to maintain a near-normal daily routine. Both basal and bolus volumes must be delivered in precise doses according to individual prescription, since an overdose or underdose of insulin could be fatal.

The first generation of portable insulin pumps refers to a "pager-like" device with a reservoir contained within a housing. A long tube is provided for delivering insulin from the pump attached to a patient's belt to a remote insertion site. The reservoir, delivery tube and the hypodermic cannula altogether constitute an "infusion set". The recommended time for replacing an infusion set is every 2-3 days to avoid local infection at the cannula insertion site. Most users, however, extend this period until the reservoir is empty, sometimes up to 7 days. Examples of such devices are disclosed in U.S. Pat. Nos. 3,631,847, 3,771,694, 4,657,486, and 4,544,369. These devices represent a significant improvement over multiple daily injections but suffer from major drawbacks, including large size, heavy weight and long tubing. The size and weight of these devices is primarily attributable to the size and number of batteries (i.e., AA or AAA-type) employed in the devices for supplying the required high energy demand of the motor, screen, alarms, and other components which consume energy.

These bulky devices with long tubes are uncomfortable and are rejected by the majority of users because they interfere with daily activities, e.g., walking, running, and sports. To avoid the tubing limitations, a second generation concept was proposed, directed to a remote controlled skin adherable device with a housing having a bottom surface adapted to be in contact with the patient's skin, with a reservoir contained within the housing, and with an injection needle adapted for fluid communication with the reservoir. These skin adherable devices are designed for replacement every 2-3 days similarly to the currently available pump infusion sets. Most patients, however, prefer to extend this period until the reservoir is empty. This concept is discussed in U.S. Pat. Nos. 4,498,843, 5,957,895, 6,589,229, 6,740,059, 6,723,072, and 6,485,461.

These second generation skin adherable devices still have at least two major drawbacks:
  The entire device should be disposed every 3 days including all expensive components (e.g., electronics, driving mechanism).
  The device is still heavy and bulky, which is exceptionally important drawback because the device should be directly attached to the patient's skin and remain in place for at least 3 days. The main reason for the large size and heavy weight is the size and number of batteries (e.g., AA, AAA or button-type) that supply energy to the motor, alarms, and maintain a communication link between the skin adherable device and the remote control unit. For example, the voltage required by many of the low voltage controllers and motors is 3 Volts, while the output of the batteries is less than 1.6 Volts.

In U.S. Pat. No. 7,144,384 to Gorman et al., assigned to Insulet Corporation, a skin adherable device is disclosed. The patent discusses that a large portion of the device is occupied by four silver-oxide button batteries positioned perpendicular to the longitudinal axis of the device, making the device thick (18 mm) and bulky. Moreover, due to high energy consumption, such batteries typically last only 3 days, forcing the user to dispose of the entire device every 3 days.

A third generation skin adherable device was devised to increase patient customization. An example of such a device is described in the co-owned, co-pending U.S. patent application Ser. No. 11/397,115 and International Patent Application No. PCT/IL06/001276. This third generation device contains a remote control unit and a skin adherable patch unit (also referred to as "dispensing patch unit") that includes two parts:
  Reusable part—containing the metering portion, electronics, and other relatively expensive components. Disposable part—containing the reservoir and in some embodiments, batteries.
  A tube delivers the fluid from the reservoir to an exit port that contains a connecting lumen.

This concept provides a cost-effective skin adherable device and allows for a diversity of features, including various reservoir sizes and various needle and cannula types.

In the co-owned, co-pending U.S. patent application Ser. No. 12/004,837 and International Patent Application No. PCT/IL2007/001578, a fourth generation device is disclosed. This device is configured as a patch that can be disconnected and reconnected to a skin adherable cradle unit. The patch can be remotely controlled or can be operated by buttons that are located on the patch as disclosed in the co-pending, co-owned U.S. Provisional Patent Application No. 60/961,527. In this configuration, the user can deliver a required bolus dose by repetitive button pressing according to a predetermined dose per button press ("Bolus buttons").

The co-owned, co-pending U.S. patent application Ser. No. 11/706,606, the disclosure of which is incorporated herein by reference in its entirety, discloses a device that contains a dispensing patch unit and an analyte sensing means (e.g., sensor). This dual function device has the same configuration that was outlined above and can also be disconnected and reconnected at the patient's discretion.

Both third and fourth generation devices may use a single, small-sized battery. An example of such a battery is a zinc-air battery, as disclosed in co-pending, co-owned U.S. Provisional Application No. 60/961,484. These batteries have many advantages, including low weight, small size, low cost, long shelf lives, high specific energy and high stability. However, such batteries have a limited amount of stored energy of about 0.3 W·h, while a single use zinc-carbon AA battery has stored energy of about 1.2 W·h AAA batteries, however, are more than ten times larger and heavier than zinc-air batteries. Therefore, in order to enable employment of a small size power source, which has limited stored energy, the energy consumption of the electrical components of the dispensing patch should be reduced, especially the energy consumption of the motor, which is the primary energy consumer.

The motor requires a substantial amount of energy for its operation: a current of about 500 mA and voltage of about 3 Volts, i.e., 1.5 Watts of electrical power. The power output of a zinc-air battery provides an electrical current of 10 mA and voltage of about 1.2 Volts, i.e., 0.012 Watts of electrical power. To provide the 3 Volts required by the motor and the CPU from a battery output of 1.2 Volts, a DC-DC step-up converter is used. The current requirements are provided by a pulsed power method, i.e., accumulating energy over a relatively long period of time and releasing it very quickly, thereby increasing the instantaneously supplied power. As such, the pulsed method is based on generating periodic pulses of high power.

It is, therefore, essential that the pulses' parameters (e.g., duty cycle, pulse duration, width and amplitude) comply with the electromechanical properties of the motor (e.g., load, torque friction). This can be carried out, for example, by changing pulse duration according to the load on the motor, as discussed in U.S. Pat. No. 5,774,426 to Mai Xuan Tu et al. The electrical load on the motor is measured to determined missed steps of the motor (i.e., momentary failure of the motor). The energy supply to the motor is increased upon detection of the missed steps. Unfortunately, this invention is applicable only to a single phase step motor and it may require several iterations (including additional missed steps of the motor and loss of energy) prior to actual supplying energy sufficient to rotate the motor.

Another method to control the motor electronically is based on changing the duty cycle according to energy stored in an implanted infusion device power source, as discussed in U.S. Pat. No. 7,122,026 to Rogers et al. The duty cycle is increased to compensate for power source depletion. Yet, some energy supply devices (e.g., zinc-air batteries) maintain nearly constant power supply even when depleted. Thus, applying this method would result in unnecessary energy consumption. This method also ignores other mechanical factors associated with the motor's operation, such as inertia and load.

SUMMARY

A device for the delivery of fluid to a patient's body is provided. The device may include a miniature and thin portable programmable fluid dispensing unit. The dispensing unit may be a small, low cost, portable dispensing patch unit which is adherable to the patient's body. The dispensing unit may include two-parts: a disposable part and a reusable part. A power source may be incorporated into the infusion device and may include without limitation a single, small-sized, button battery.

In some embodiments, the dispensing unit includes a driving mechanism and pumping mechanism to dispense fluid from a reservoir to an outlet port that can be connected to a cannula subcutaneously inserted in the patient's body.

The device includes a motor (e.g., stepper motor or DC motor) requiring energy for its operation. The amount of required energy may include a current of about 500 mA and voltage of about 3 Volts, i.e., 1.5 Watts of electrical power. A zinc-air battery provides a current of 10 mA and, voltage of about 1.2 Volts, i.e., 0.012 Watts of electrical power. To provide the 3 Volts required by the motor and CPU from a battery output of 1.2 Volts, a DC-DC step-up converter is used. The current requirements are provided by a pulsed power method, i.e., accumulating energy over a relatively long period of time in a high capacity capacitor and releasing it very quickly, thus, increasing the instantaneous current and generating high power pulses for a short period of time. The motor is provided with a sequence of customized pulses, also referred to as a pulse train, each pulse being characterized by its current, width, duty cycle and frequency. Each pulse's width is adjusted to fulfill the power requirements of the motor, i.e., when changing the motor rotational velocity (e.g., during acceleration or slow down), the pulses are wider than pulses associated with constant rotational velocity. It should be noted that although a stepper motor rotates in a fixed angle with each pulse provided to it, the motor output (e.g., torque or steps per second) can be adjusted by customizing the pulses. For example, short duration pulses (e.g., 0.4-0.6 milliseconds) will result in higher rotational velocity compared to long duration pulses (e.g., 0.9-1.2 milliseconds).

In some embodiments, the motor is provided with pulsed power that is adjustable according to its rotational velocity. In turn, when the motor velocity changes, more power is provided to overcome the friction and inertia of the driving mechanism or pumping mechanism. On the other hand, when the velocity remains constant, only minimal power is supplied because only minor forces are exerted upon the driving mechanism or pumping mechanism. These forces may be utilized for stopping the pumping mechanism, and thereby less power would be required to stop the motor. The motor rotational velocity can be measured by counting the motor's revolutions per time unit as described in the co-owned, co-pending International Patent Application No. PCT/IL2008/000642, filed May 11, 2007, and entitled "Methods and Apparatus for Monitoring Rotation of an Infusion Pump Driving Mechanism," the disclosure of which is incorporated herein by reference in its entirety. In some embodiments, the motor may utilize a step-up voltage converter and pulsed power mechanism.

In some embodiments, the device may include a miniature energy source which is a sufficient energy source by virtue of a dedicated energy saving method employed for controlling a motor driver. Such may consider the driving mechanism's inertia and be implemented regardless of motor type, battery, pumping mechanism and other parameters and characteristics of the device.

In some embodiments, the device may employ an energy saving mode for the operation of the dispensing unit.

In some embodiments, a power supply mode may exploit the rotational inertia of the motor or pumping mechanism to save energy. In other embodiments, the power supply mode may exploit friction forces applied to the motor or pumping mechanism for saving energy.

In some embodiments, implementing the pulsed power method by using a low power source (e.g., zinc-air battery) and energy storage device (e.g., capacitor), the motor cannot rotate for a long period of time without a controller (e.g., CPU). This safety mechanism inherently restricts an uncontrolled motor rotation which may result in drug overdose, fatal to the patient.

In some embodiments, the device includes a miniature dispensing unit having a small and low power battery that is sufficient to supply energy for the entire usage duration.

It is an object of some embodiments to provide accurate control of the motor's rotation while employing an energy saving mode.

It is an object of some of embodiments to provide a method to control the pulse parameters of the motor to save energy during the motor operation.

The foregoing and other features, aspects, and advantages of the present invention will be more apparent from the following detailed description.

BRIEF DESCRIPTION OF THE DRAWINGS

FIGS. 1*a-c* show a single-part dispensing unit (FIG. 1*b*), a two-part dispensing unit (FIG. 1*c*) and a remote control unit.

FIG. 17 is a plot illustrating an example of a pulse train implementing the rotational velocity shown in FIG. 11*a*.

DETAILED DESCRIPTION

A dispensing unit (10) and a remote control unit (40) are described herein. In some embodiments, the dispensing unit (10) may include a single part (as shown in FIG. 1*b*) or two parts (as shown in FIG. 1*c*). The two-part dispensing unit includes a reusable part (100) and a disposable part (200). The dispensing unit (10) may employ different dispensing mechanisms, including without limitation a syringe-type reservoir with a propelling plunger, peristaltic positive displacement pump In some embodiments, the dispensing unit (10) can be adhered to the patient's body by a skin adherable cradle unit. An example of such a cradle unit is disclosed in the co-owned, co-pending U.S. patent application Ser. No. 12/004,837 and International Patent Application No. PCT/IL2007/001578, the disclosures of which are incorporated herein by reference in their entireties. The term "dispensing unit" is not limited to fluid delivery. In some embodiments, the dispensing unit (10) may be capable of dispensing fluid (e.g., insulin) to a patient's body or sensing analyte (e.g., glucose) in the body.

Infusion programming, data transferring and control of the dispensing unit (10) can be carried out by a remote control unit (40), which may be configured as a personal digital assistant ("PDA"), a hand watch, a cellular phone, or any other means. The remote control unit (40) is capable of establishing a unidirectional communication with the dispensing unit (10), i.e., the remote control unit (40) only transmits data to the dispensing unit (10) or only receives data from the dispensing unit (10). The communication link between remote control unit (40) and dispensing unit (10) can be also bidirectional, i.e., the remote control unit (40) is capable of transmitting and receiving data to and from the dispensing unit (10).

Figure 2A:
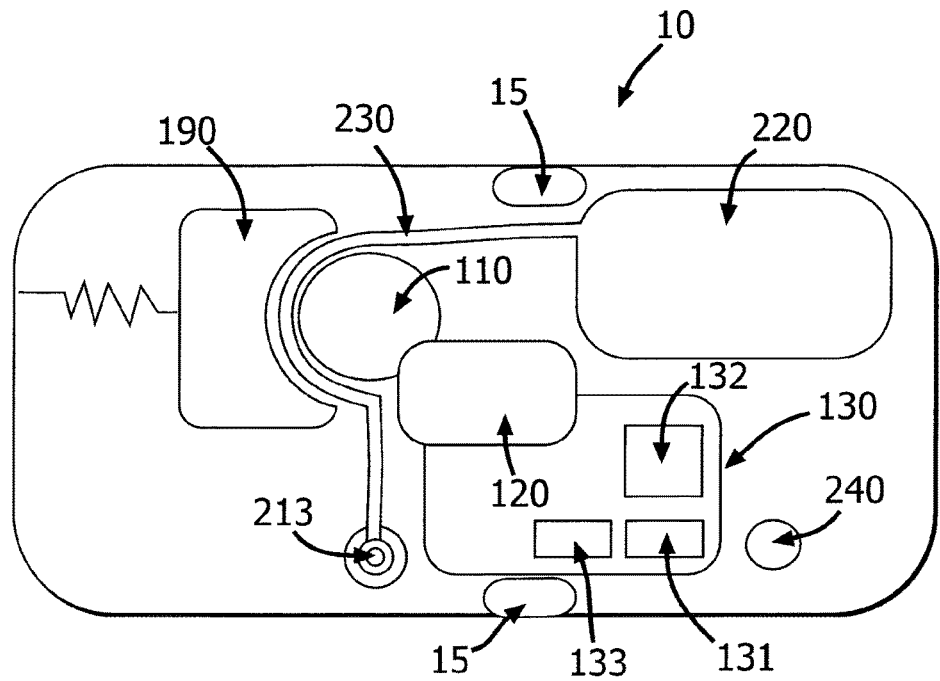
FIGS. 2*a-b* show a single-part dispensing unit (FIG. 2*a*) and a two-part dispensing unit (FIG. 2*b*) employing a peristaltic pumping mechanism.
Figure 2B:
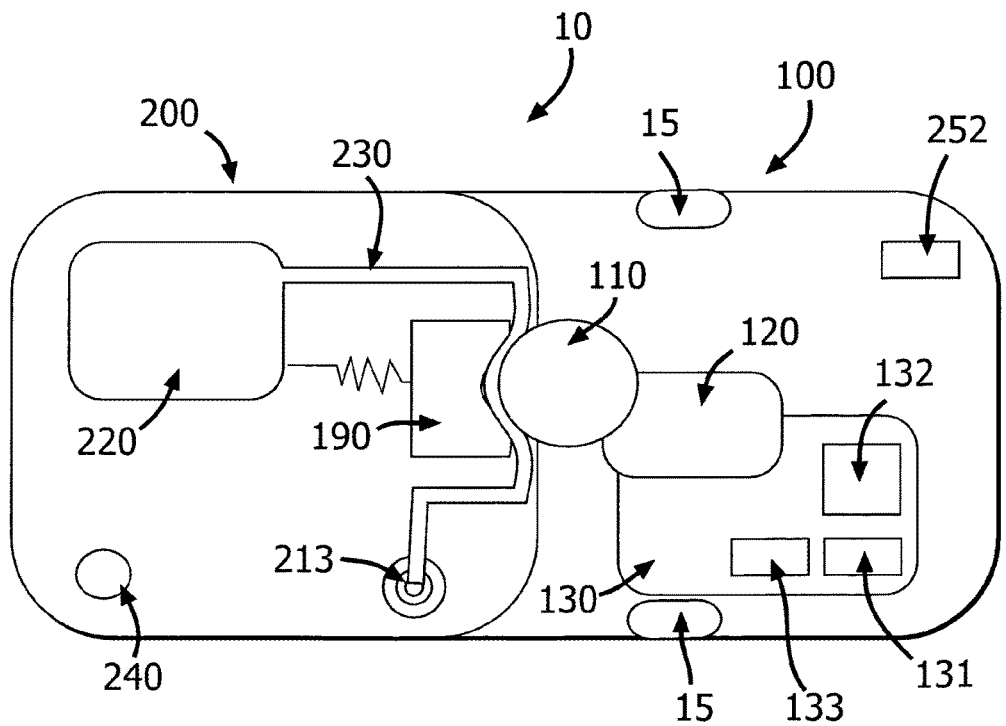

FIGS. 2*a-b* show exemplary embodiments of the dispensing unit (10) employing a peristaltic pumping mechanism for dispensing fluid to a user's body. FIG. 2*a* shows a single-part dispensing unit (10). The fluid is delivered from a reservoir (220) provided in the dispensing unit (10) through a delivery tube (230) to an exit port (213). The peristaltic pump includes a rotary wheel (110) provided with rollers (not shown) and a stator (190). Rotation of the rotary wheel (110) and periodic squeezing of the delivery tube (230) against the stator (190) positively displaces fluid from the reservoir (220) to the exit port (213). An example of such a positive displacement pump is disclosed in the co-owned, co-pending U.S. patent application Ser. No. 11/397,115, filed on Apr. 3, 2006, the disclosure of which is incorporated herein by reference in its entirety. A driving mechanism (120) for rotating the rotary wheel (110) can be provided. The driving mechanism (120) includes a gear and a motor. The motor can be a Stepper motor, a DC motor, SMA actuator or any other motor. The driving mechanism (120) is controlled by electronic components (130) residing in the dispensing unit (10). The electronic components (130) may include a controller (not shown), a processor (132), a transceiver (131) and/or a transmitter (133). An appropriate power source (240) and an energy storage device (252) (e.g., a capacitor) are also provided. The power source (240) may include without limitation one or more batteries, such as a button-sized zinc-air battery.

In some embodiments, the power source (240) may be a button battery and the energy storage device (252) may be a high capacity (e.g., about 0.2 F) capacitor. Using a button battery usually requires the supply of pulsed power in order to increase the current output by the battery. The pulsed power mode is established by periodically charging and discharging the high capacity capacitor. Infusion programming of the dispensing unit (10) can be carried out either by remote control unit (40) and/or by manual buttons (15) provided on the dispensing unit (10).

FIG. 2b shows a two-part dispensing unit (10) that includes a reusable part (100) and a disposable part (200). The reusable part (100) includes a positive displacement pump provided with rotary wheel (110), driving mechanism (120), and electronic components (130). The disposable part (200) includes reservoir (220), delivery tube (230), power source (e.g., button battery) (240), energy storage device (252), exit port (213), and stator (190). Pumping is enabled upon attachment of the two parts to each other. This arrangement is discussed in the co-owned, co-pending U.S. patent application Ser. No. 11/397,115, filed on Apr. 3, 2006, the disclosure of which is incorporated herein by reference in its entirety. The power source (240) may also be located in the reusable part (100) and can be rechargeable.

Figure 3A:
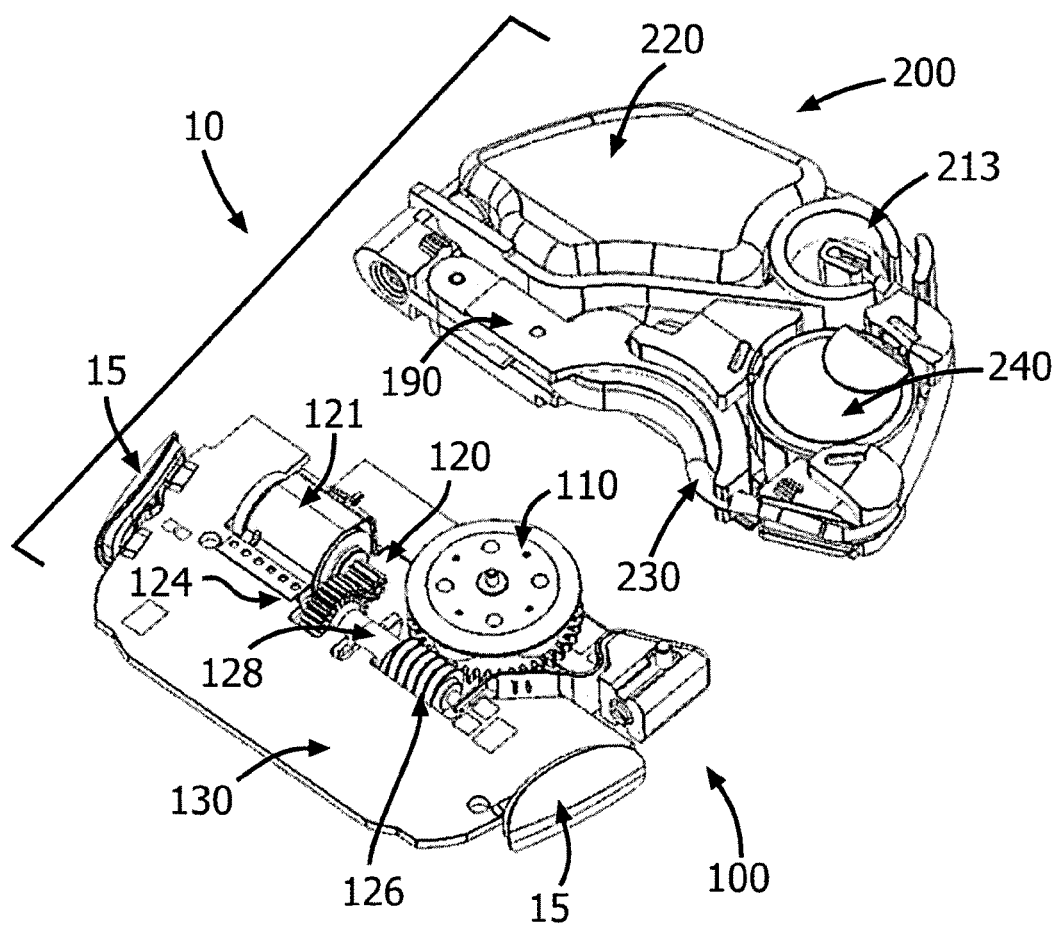
FIGS. 3*a-b* show a two-part dispensing unit employing a peristaltic pumping mechanism.
Figure 3B:
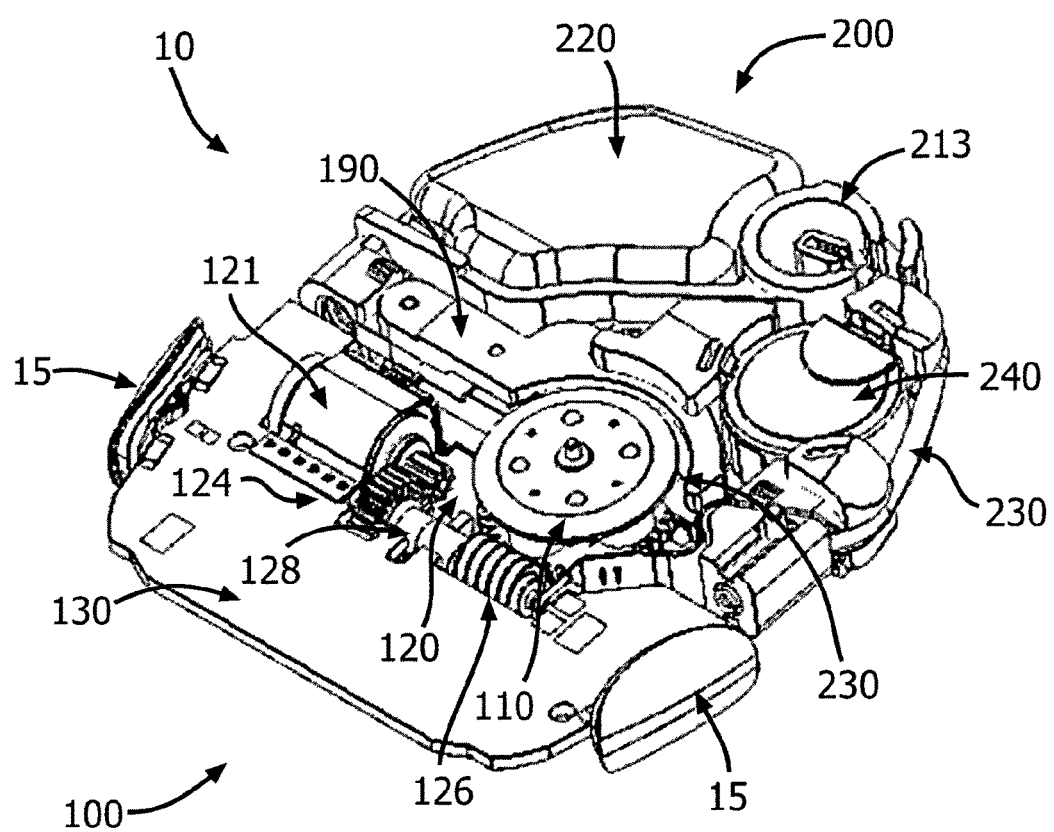

FIGS. 3a and 3b show respectively an embodiment of the two-part dispensing unit (10) prior to (as shown in FIG. 3a) and subsequent to (as shown in FIG. 3b) connection of the two parts. The reusable part (100) contains a peristaltic pumping mechanism provided with rotary wheel (110) and a driving mechanism (120) having a motor (121), a worm (126), a shaft (128) and gears (124). The reusable part (100) also contains electronic components (130). The disposable part (200) includes reservoir (220), delivery tube (230), power source (240), exit port (213), and stator (190). The power source (240) may be a zinc-air battery or button battery.

Figure 4A:
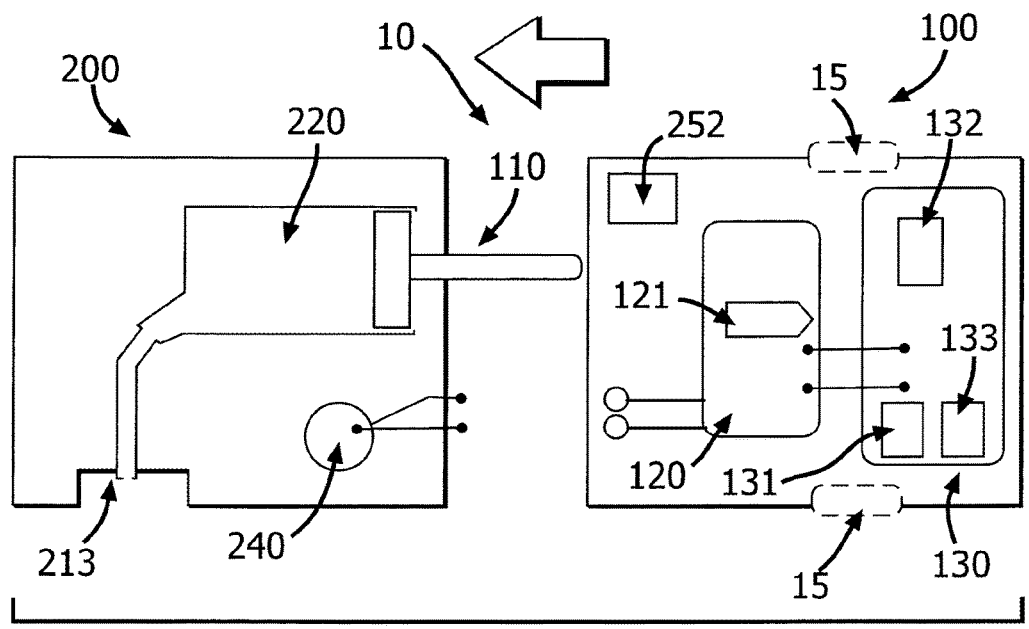
FIGS. 4*a-b* show a single-part dispensing unit (FIG. 4*b*) and a two-part dispensing unit (FIG. 4*a*) employing a syringe-piston pumping mechanism.
Figure 4B:
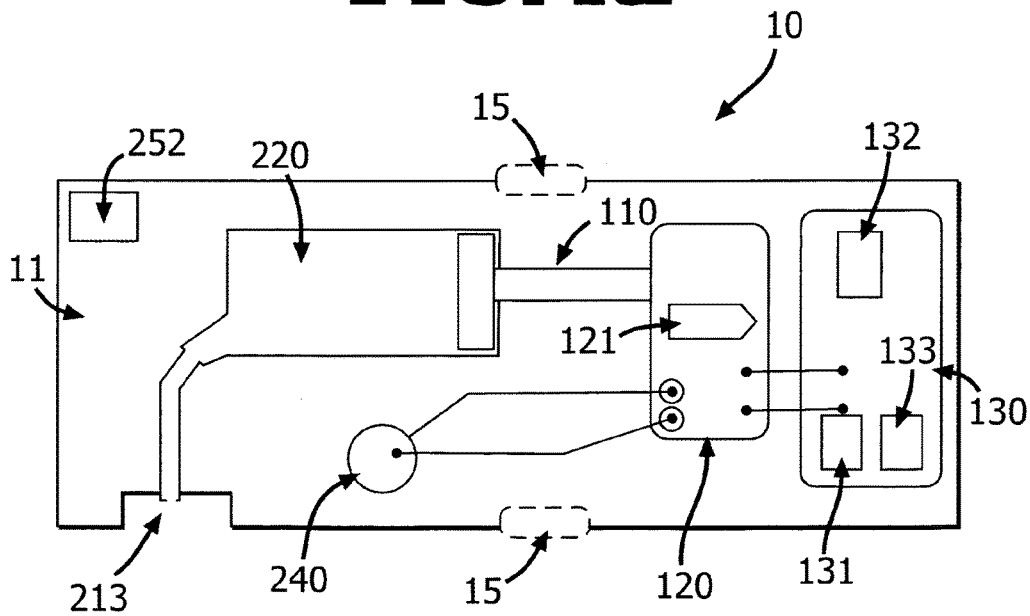

FIGS. 4a-b show embodiments of the dispensing unit (10) employing a piston-plunger pumping mechanism for dispensing fluid to a user's body. FIG. 4a shows a two-part dispensing unit (10) having a reusable part (100) and a disposable part (200). The disposable part (200) includes reservoir (220) provided with plunger assembly (110), power source (e.g., battery) (240), energy storage device (252), and exit port (213). In alternative embodiments, the plunger assembly (110) may be located in the reusable part (100) or be shared by both parts. The reusable part (100) includes a driving mechanism (120), which has a motor (121) (e.g., Stepper motor, DC motor, or SMA actuator) and a driving gear (not shown) for displacing the plunger assembly (110). The driving mechanism (120) is controlled by electronic components (130), which has a controller (not shown), a processor (132), a transceiver (131), and/or a transmitter (133). Infusion programming can be carried out by a remote control unit (not shown) and/or by one or more buttons (15) provided on the dispensing unit (10). The power source (240) may be located in the reusable part (100) and may be rechargeable. An example of such a dispensing unit is disclosed in the co-owned, U.S. Provisional Patent Application No. 61/123,509, filed on Apr. 9, 2008, the disclosure of which is incorporated herein by reference in its entirety.

FIG. 4b shows a single-part dispensing unit (10), which includes substantially similar components as the two-part dispensing unit (10). The components of the single-part dispensing unit (10) are deployed within a common housing (11). The embodiments shown in FIGS. 4a-b are disclosed in the co-owned, co-pending International Patent Application No. PCT/IL2008/000641, the disclosure of which is incorporated herein by reference in its entirety.

Figure 5:
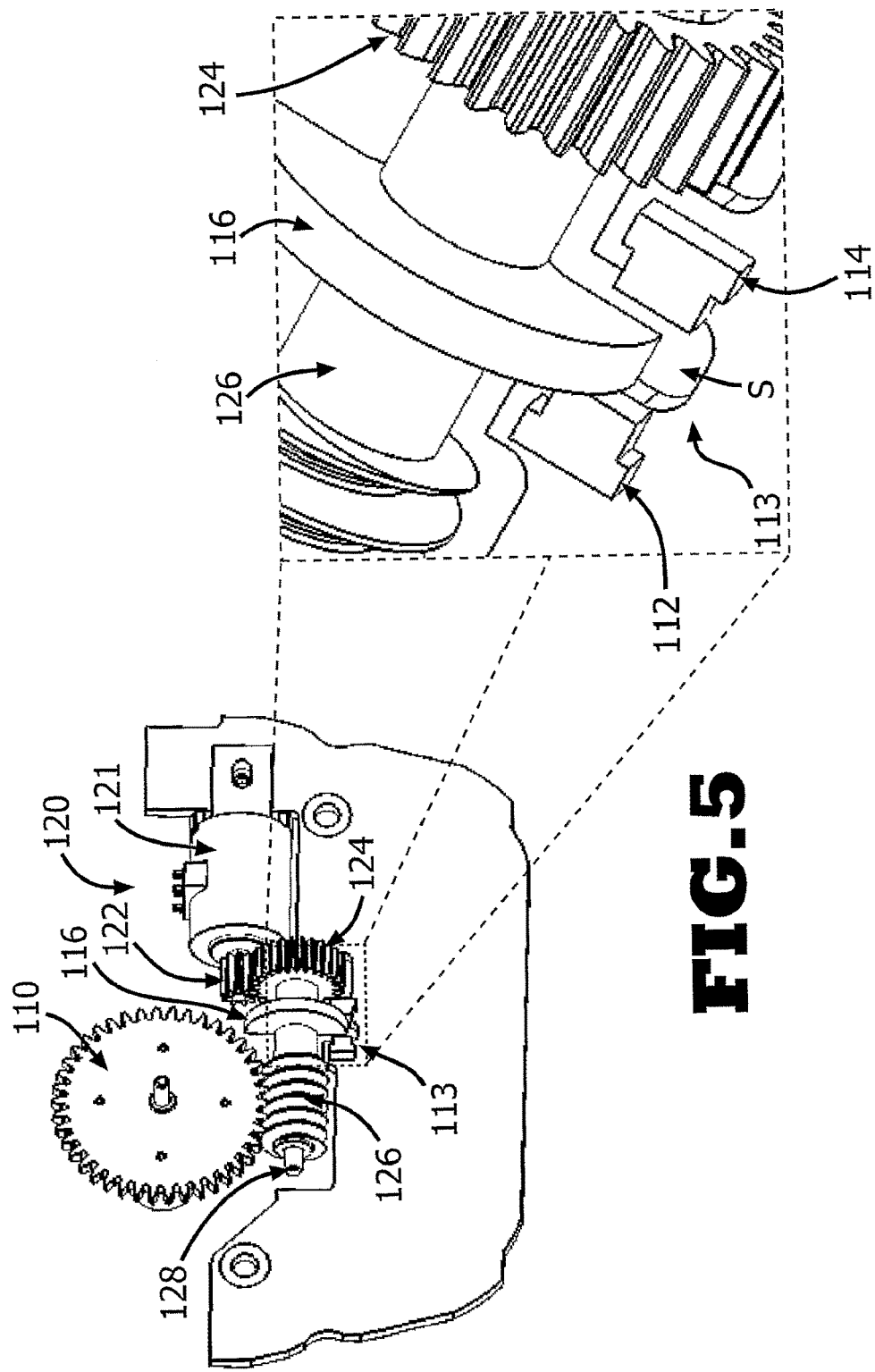
FIG. 5 shows a sensing and monitoring device for the control of rotational movements of the driving mechanism and pumping mechanism.

Any of the above-mentioned embodiments may be provided with a sensing and monitoring device for controlling operation of the driving mechanism (120). FIG. 5 shows this device employing a photo interrupter (113) as disclosed in the co-owned, co-pending International Patent Application No. PCT/IL2008/000642, the disclosure of which is incorporated herein by reference in its entirety. The sensing and monitoring device is provided with an encoder vane (116) configured as a 180 degree sector, which is affixed to a shaft (128) such that the encoder vane (116) rotates with the shaft (128) at the same rotational velocity. Photo-interrupter (113) is positioned such that as encoder vane (116) rotates it passes through space (S) between LED (112) and light detector (114). The motor's (121) rotational velocity can be derived from the shaft's (128) rotational velocity by taking into consideration the gear (124) reduction ratio. For example, when the shaft (128) rotates at 1 rotation per minute (RPM) and the gear (124) ratio is 3:1; the motor's (121) speed is 3 RPM. Other sensing and monitoring devices may also be employed to measure the motor's (121) rotational velocity.

Figure 6:
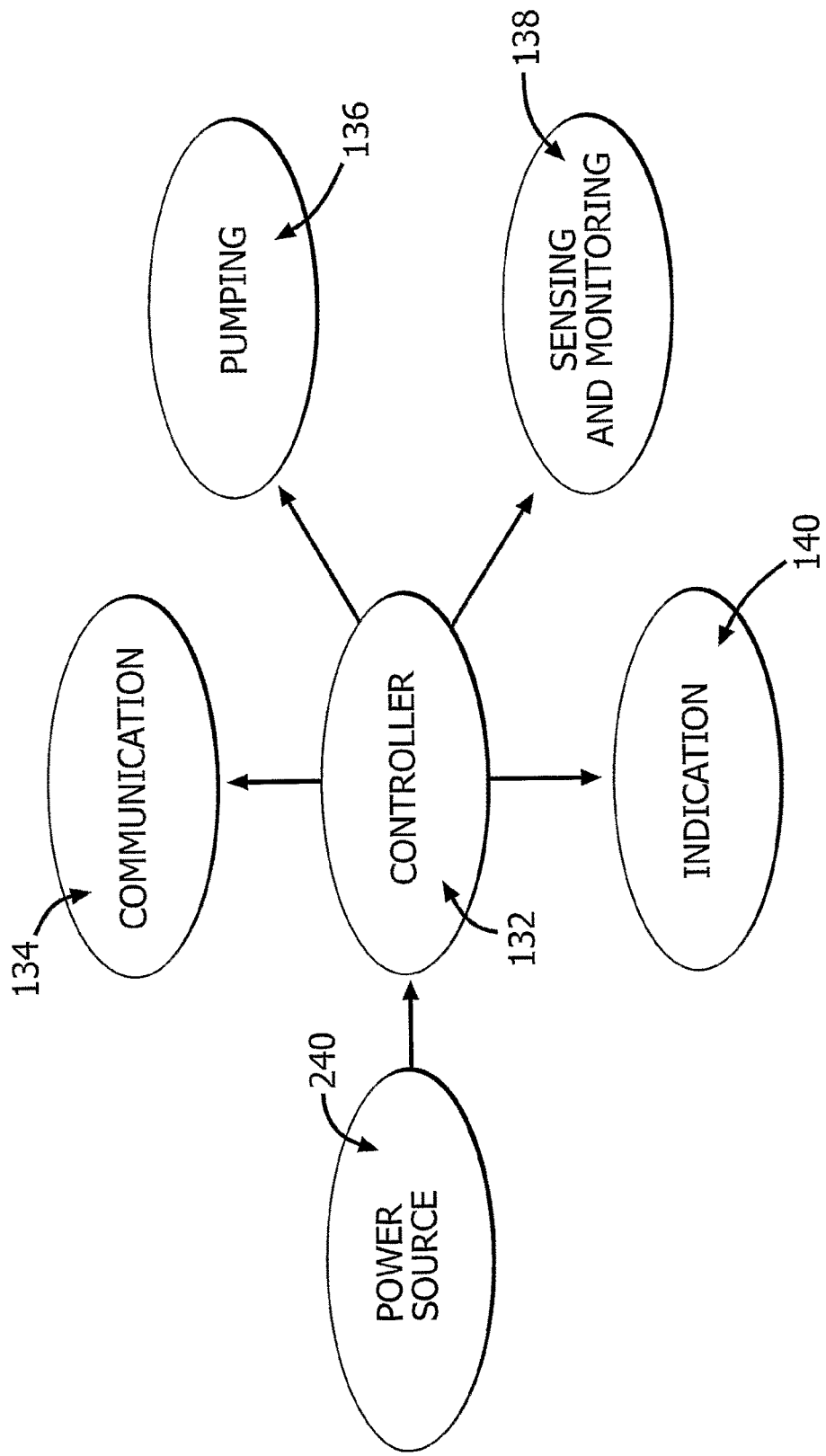
FIG. 6 shows a block diagram of the dispensing unit including energy suppliers and consumers.

FIG. 6 shows schematically the power source (240) and energy consuming components of the dispensing unit (10) controlled by controller (132). The energy consuming components include:

- a communication device (134), which may include without limitation RF, IR and other communication types (e.g., magnetic relay, manual buttons, audible commands).
- a pumping mechanism (136) actuated by a driving mechanism having a motor and motor driver.
- a sensing and monitoring device (138), which may include without limitation an occlusion sensor or motion sensor.
- an indication device (140), (also referred to as "notification device"), which may include without limitation a buzzer or vibration alarm.

Figure 7:
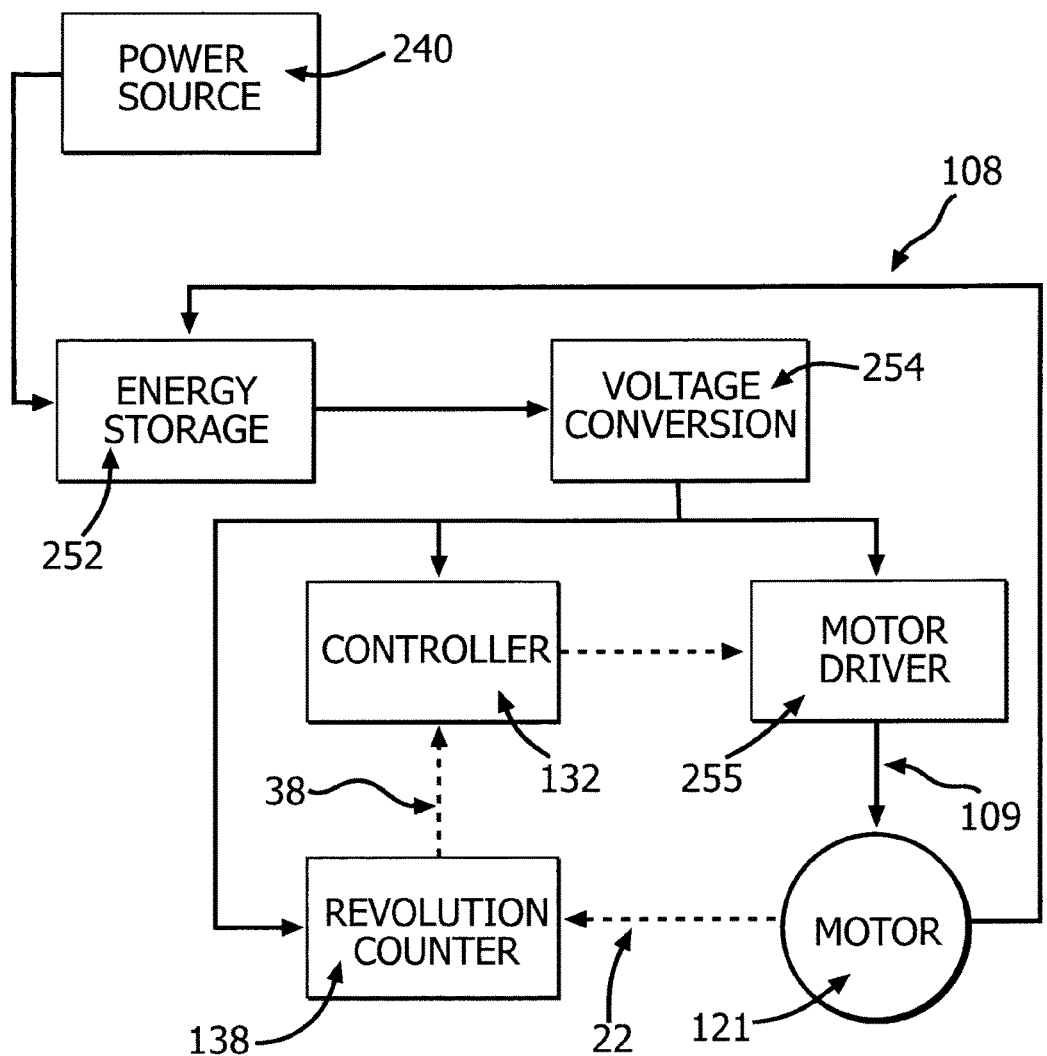
FIG. 7 shows a block diagram of an energy supply and motor control of the dispensing unit.

FIG. 7 shows a flow chart depicting an energy supply and control of the motor (121). In practice, a low price, small-sized power source (240) (e.g., button battery) may be used, particularly a small quantity thereof, to provide a dispensing unit (10) that is of miniature size and lightweight. Due to the small size of a button battery, the electrical power output produced thereby, i.e., current ("i") and voltage ("v"), is substantially lower than the electrical power required for motor operation, i.e., a condition is satisfied whereby $$i_{battery} \cdot v_{battery} << i_{motor} \cdot v_{motor} \text{ or } W_{battery} << W_{motor}$$

For example, a zinc-air battery has a maximum power output of about 0.03 Watts (e.g., current of about 25 mA and voltage of about 1.2 Volts), while the motor (121) requires electrical power of 1.5 Watts (e.g., current of about 500 mA and voltage of about 3 Volts). It can be seen in this example that the electrical power ($W_{motor}$) required the motor is times larger than what battery ($W_{battery}$) is able to supply. The electric power required by the motor is not limited to the particular electrical power indicated above.

Thus, in order to enable operation of the motor (121), the voltage and current supplied thereto are increased. Voltage increase can be carried out by virtue of a DC-DC converter (254) which can for example convert the 1.2 Volts supplied by the battery, i.e., power source (240), to the voltage required by the motor (121), i.e., 3 Volts. Increasing the current can be carried out by a pulsed power method, i.e., by charging the energy storage device (252) (e.g., a 0.2 F capacitor) for approximately 1 second and then discharging it for about 20 milliseconds. This enables multiplication of the current by 50 times.

The 3V voltage is also supplied to the controller (132) and to the sensing and monitoring device (138) (e.g., revolution counters). Such a sensing and monitoring device (138) is disclosed in the co-owned, co-pending International Patent Application No. PCT/IL2008/000642, as noted above. The motor driver (255), which is controlled by the controller (132), operates the motor (121) by providing it with a pulsed power, as shown by line (109). The pulsed power is supplied by the energy storage device (252).

In some embodiments, the motor's (121) operation is controlled by the principle of a closed-loop feedback, according to which the amount of power supplied to the motor (121) is adjusted based on the motor's (121) rotational velocity (38). Sensing and monitoring device (138) (e.g., revolution counter or rotation sensor) measures the motor's (121) output as shown by dashed line (22) and provides the controller (132) with the required data, including without limitation, the motor's (121) instant rotational velocity, as shown by dashed line (38). In some embodiments, the sensing and monitoring device (138) merely provides a number of revolutions of the motor (121), while the velocity is calculated by the controller (132). In some embodiments, the motor's (121) mechanical energy may be converted into electrical energy, as shown by line (108). This energy can be stored in the energy storage device (252) for later use.

Figure 8A:
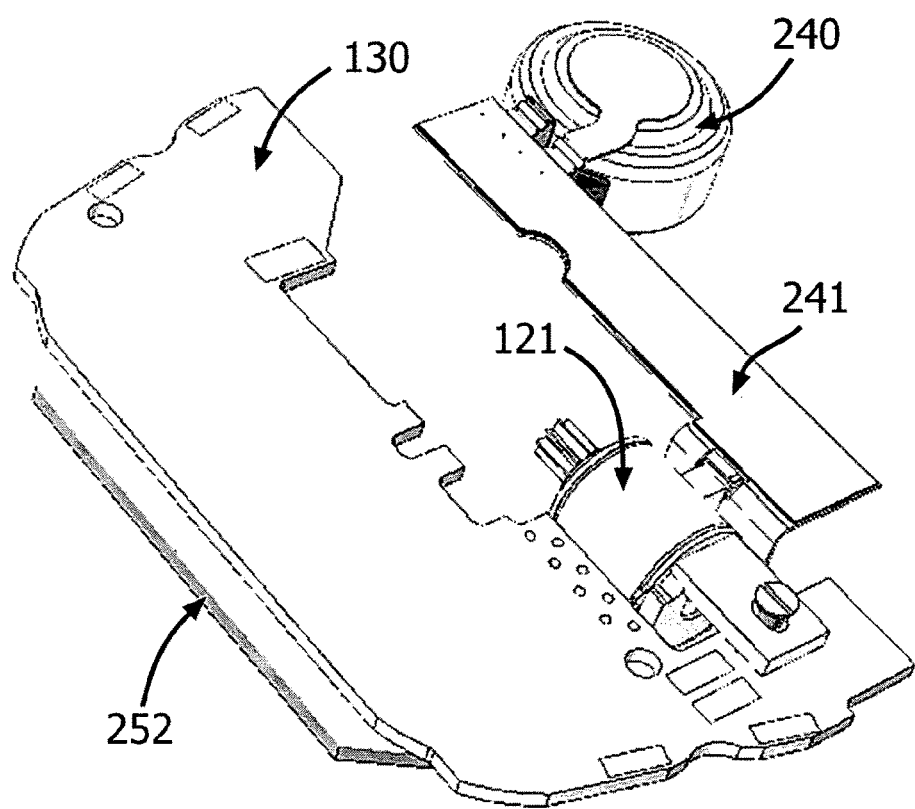
FIGS. 8*a-b* show an energy storage device for providing pulsed power.
Figure 8B:
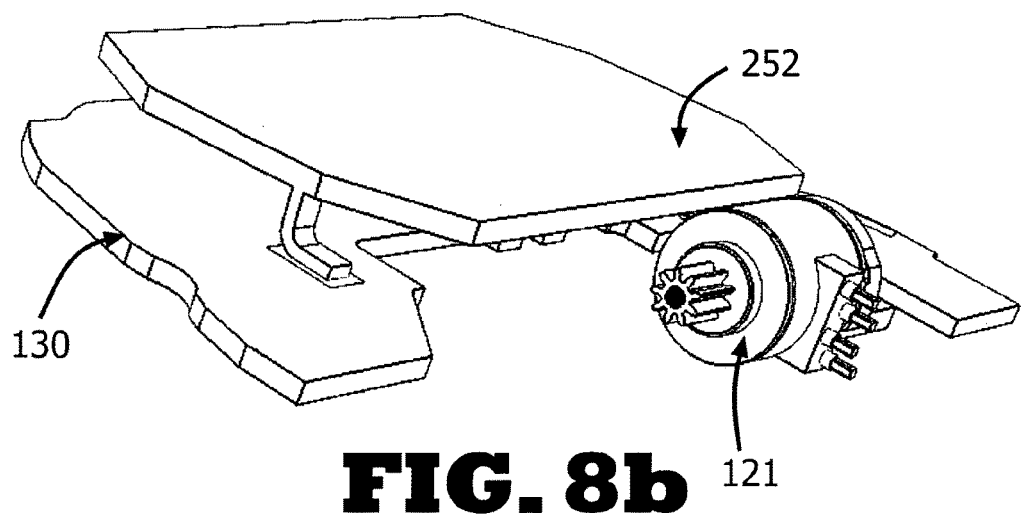

FIGS. 8a-b show the main components depicted in FIG. 7: the motor (121), the energy storage device (252), and the power source (240) connected by flat strip connectors (241) to other electrical components (130). The energy storage device (252) can be a high capacity capacitor having a capacity of 180 mF to 200 mF. It is advantageous if the capacitor has a flat configuration and reduced dimensions (e.g., 29 mm×17 mm×0.9 mm). Consequently, the capacitor may be placed parallel to the electronic components (130) (e.g., a printed circuit board), which allows the dispensing unit (10) to be kept as small and thin as possible. In practice, the capacitor having the above-mentioned configuration and dimensions provides a dispensing unit having thickness less than 15 mm.

Figure 9A:
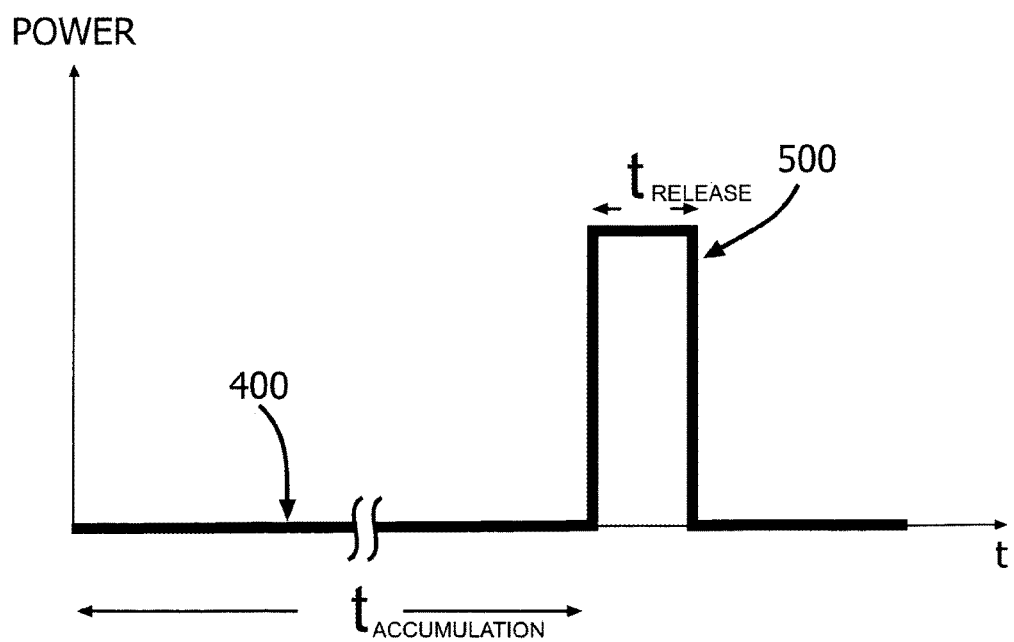
FIGS. 9*a-b* show power versus time and current versus time plots of the pulsed power supplied by a capacitor.
Figure 9B:
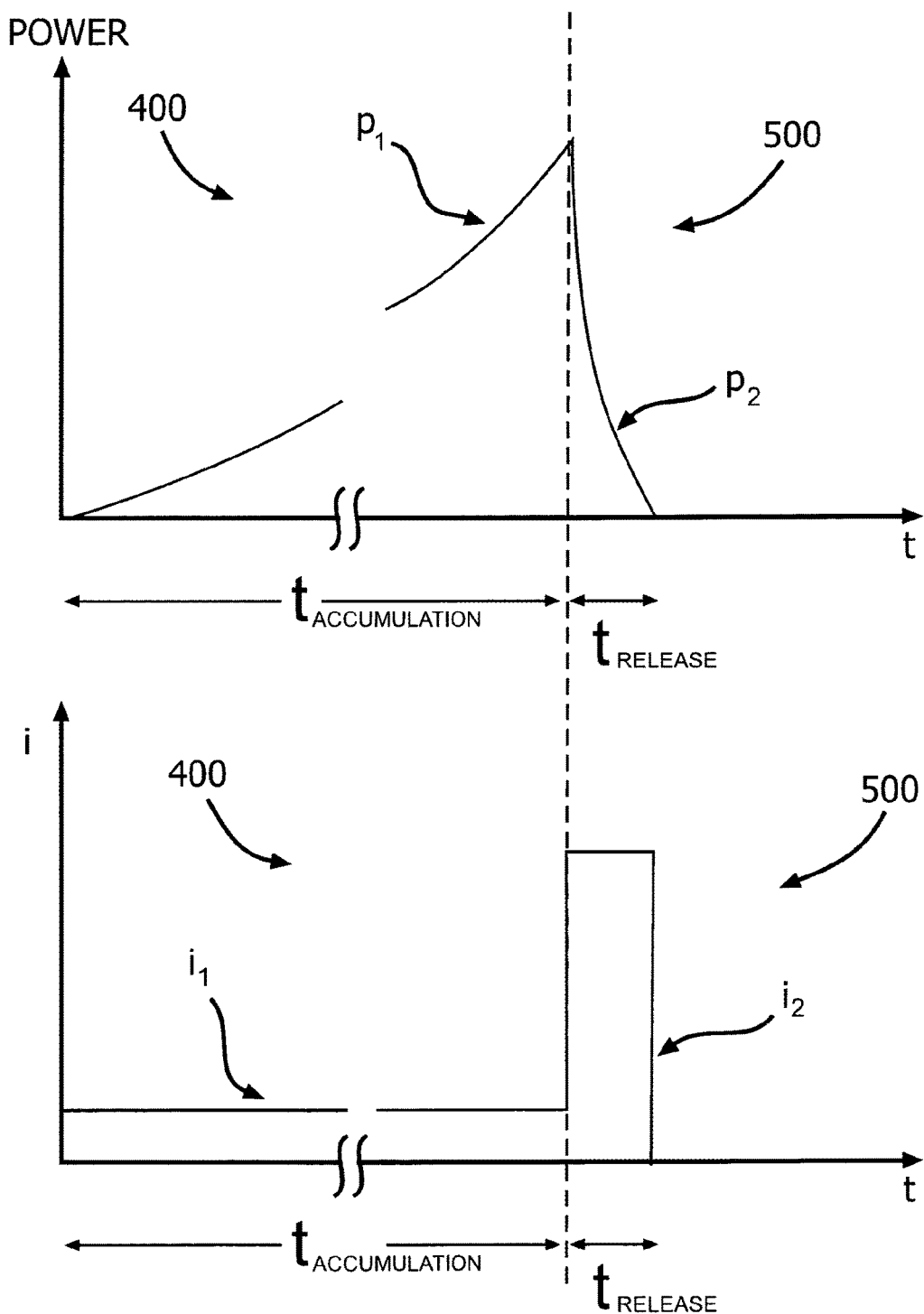

FIGS. 9a-b are power-time plots illustrating a pulsed power produced by a capacitor and supplied to the motor. In some embodiments, the supply of pulsed power includes two modes: accumulation mode (400) and release mode (500). During the accumulation mode (400), a battery charges the capacitor. During the release mode (500), the capacitor is being discharged and supplies current to power consuming components of the dispensing unit, including without limitation, the motor and electronic elements.

The ratio between the accumulation time t ("$t_{accumulation}$") and release time ("$t_{release}$") "$t_{release}$") is proportional to the ratio between the power required for operation of power consuming components, such as a motor ("$W_{motor}$") and the electrical Power outputted by a battery ("$W_{battery}$"), i.e., $$\frac{taccumulation}{trelease} \alpha \frac{Wmotor}{Wbattery}$$

FIG. 9a shows a graph of a typical charging/discharging cycle of the capacitor having the two modes. It is clear that the duration of the accumulation mode (400) is substantially longer than the release mode (500). In practice, this duration may be 50 times longer. Therefore, the maximal pulse train duration applied for activating the motor is less than the release mode (500) duration. In alternative embodiments, the charge stored in the capacitor may be monitored (e.g., by an A/D converter), thereby allowing a dynamic control over the discharging and recharging of the capacitor to be achieved.

FIG. 9b shows schematic graphs of the power ("Power") and current ("i") of a charging/discharging cycle of the capacitor. During accumulation mode (400), the energy that is supplied by the battery is accumulated and stored in the capacitor. In practice, when applying a 0.2 F capacitor and a zinc-air battery, it may take 980 milliseconds. The energy ($p_1$) that is stored in the capacitor gradually increases while the supplied current ($i_1$) remains constant. During the release mode (500), the capacitor discharges and, supplies the required amount of power to the power consuming components. When the capacitor has 0.1 F capacity and the battery is a silver-oxide button-sized battery with 0.186 Watt output, the release mode can take 10 milliseconds, while the accumulation time is about 8 times higher. Discharged power and current are designated as p2 and i2, respectively. In some embodiments, there may be continued charging of the capacitor, even during the discharge phase, which shortens the time interval between two consecutive pulses. If the capacitor is fully loaded, the charging process may not continue.

Figure 10A:
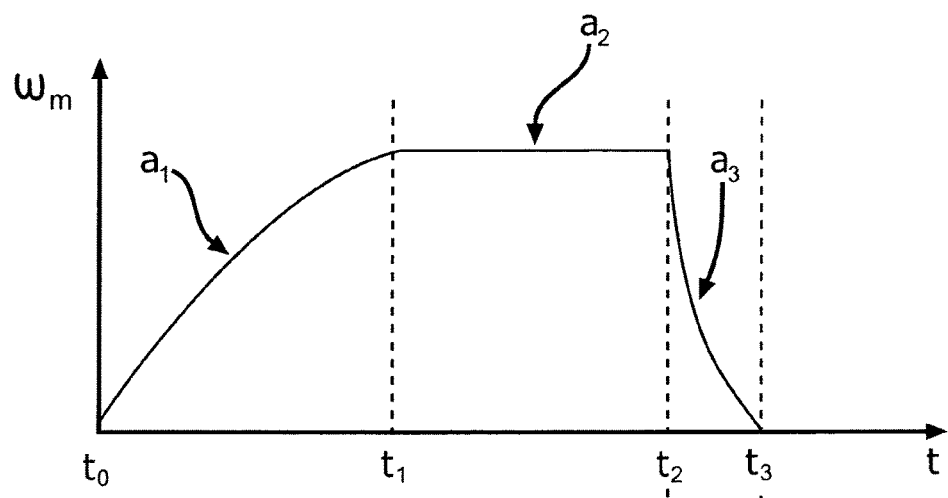
FIGS. 10*a-b* are plots illustrating rotational velocity and power profiles as a function of time as supplied to the motor.
Figure 10B:
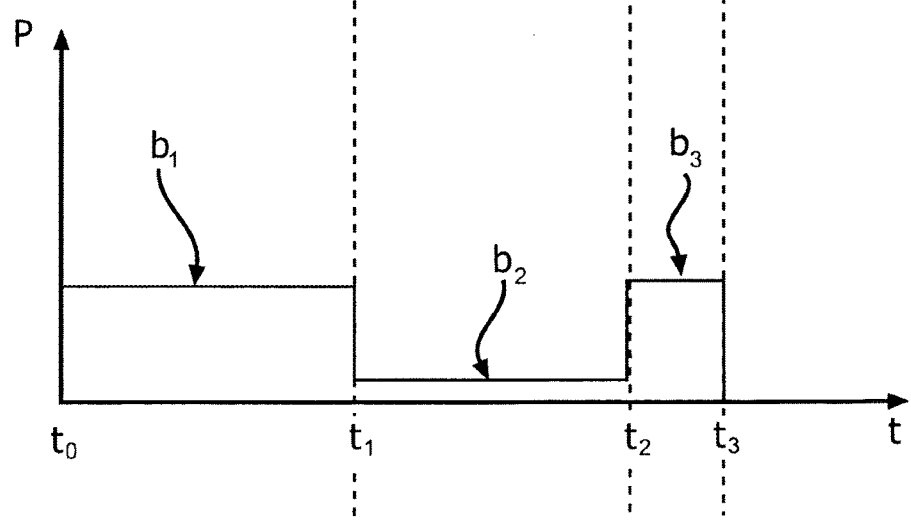

FIG. 10a shows the angular velocity ($\omega_m$) of the motor versus time (t) and FIG. 10b shows the corresponding power (P) discharged from the capacitor and supplied to the motor. During this period, the motor operates the pump to deliver fluid (e.g., insulin) via the dispensing unit. When the motor is rotated based on energy from the capacitor only a limited amount of fluid can be delivered during a single charging/discharging cycle and, therefore, more than one cycle may be required to deliver the appropriate amount of fluid required for therapeutic treatment.

In some embodiments, a variant pulse train can be supplied to the motor each time the capacitor is being discharged. The amount of power supplied during the discharge of the capacitor depends upon whether the motor rotates with constant or variable rotational velocity.

At t=$t_0$, the motor begins to rotate and its rotational velocity should be gradually increased up to a certain velocity. The increasing velocity is designated as $a_1$. The velocity increases due to supplying a certain amount of electrical power delivered by the capacitor to the motor (P>0). This power is designated as $b_1$. At t=$t_1$, the motor's angular velocity is constant, as represented on the graph in FIG. 10a as a plateau. The achieved velocity is designated as $a_2$. The amount of power required to keep the motor rotating at constant velocity $a_2$ can be $b_2$, which is less than b1 since constant angular velocity ($\omega_m$) is maintained due to inertia. Thus, the required power ($b_2$) is less than $b_1$. During the time interval from t=$t_2$ to t=$t_3$, the velocity of the motor is decreased until full stop (the decreasing velocity is designated as $a_3$). The velocity can be reduced by supplying power b3, as may be required to overcome inertia until stopping the motor. In some embodiments, the time interval from t=$t_1$ to t=$t_3$ is about 20 milliseconds.

The pattern of the pulses is typically predetermined when the pulse trains are tailored. That is, the dispensing pump is initially configured with at least one pulse train. In some embodiments, the dispensing pump controller can adjust and combine various pulses and pulse trains as needed. In other embodiments, the controller can adjust and schedule the pulse train (e.g., energy, number of pulses, width of pulses, or frequency) based on the energy stored in the energy storage device or power source.

Figure 11A:
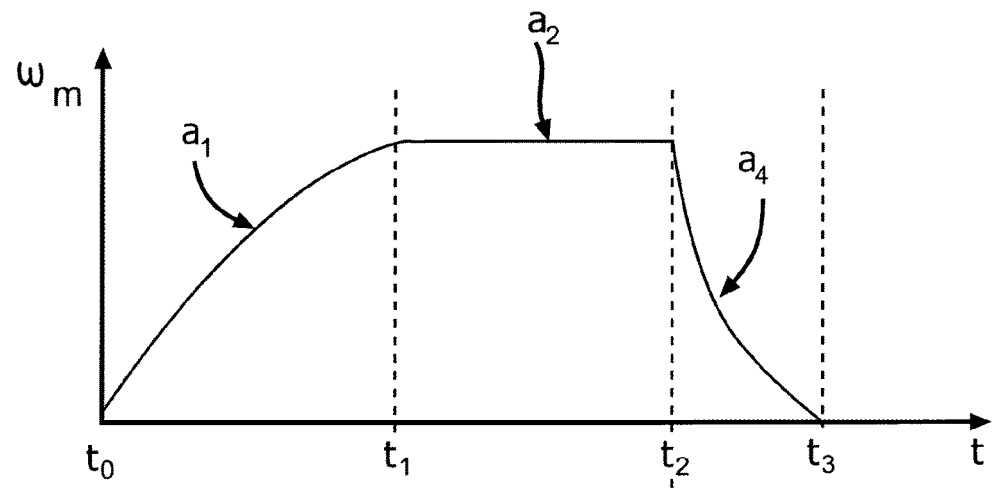
FIGS. 11*a-b* are plots illustrating alternative rotational velocity and power profiles as a function of time.
Figure 11B:
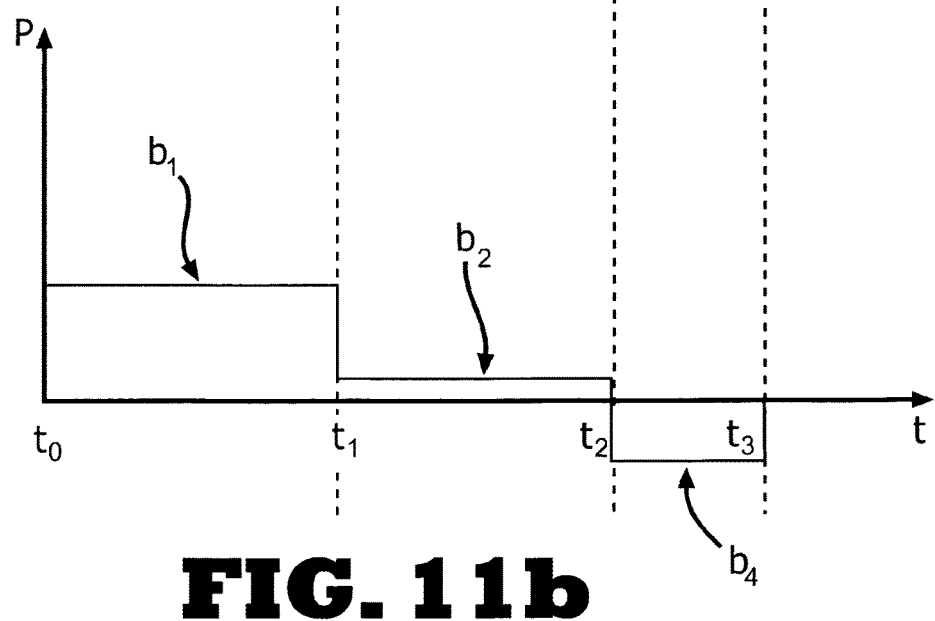

FIGS. 11a-b refer to another embodiment and show graphs of the angular velocity ($\omega_m$) of the motor versus time (t) and the corresponding power (P) required by the motor versus time (t). The graphs depict variations in velocity and power during drug delivery, while an alternative operational mode of the motor is employed for saving energy. The two first phases designated by $a_1$, $a_2$ and $b_1$, $b_2$ are identical to those referred to in FIGS. 10a-b. During the time interval starting at $t=t_2$ and ending at $t=t_3$, the velocity of the motor is decreased merely due to friction forces until a full stop (the reducing velocity is designated in FIG. 11a as $a_4$). FIG. 11b shows that in this time interval ($t=t_2$ to $t=t_3$), the motor continues to rotate and no energy is required. Therefore, energy associated with the rotation of the motor is available for use by the energy consuming components while the motor itself does not require supply of energy, i.e., during this phase the motor may operate like a dynamo.

Figure 12:
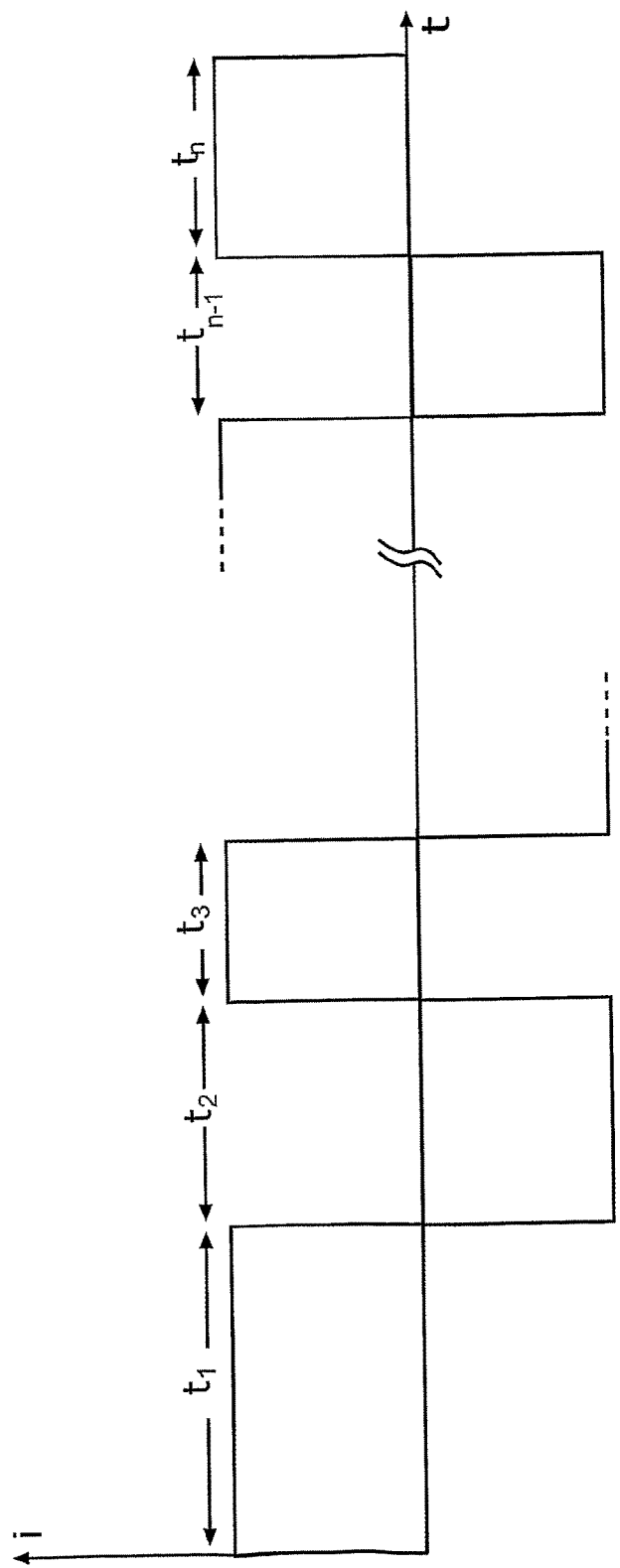
FIG. 12 is a plot illustrating a pulse distribution required for a power profile as supplied to the motor.

FIG. 12 shows current (i) supplied to the motor versus time (t), during a pulse train employing the operation mode described in FIGS. 10a-b. The current (i) is supplied by pulses while each pulse is characterized by a time interval ("t") (i.e., a period). The initial pulse (e.g., between $t_1$ and $t_2$) has long period $t_1$, typically lasting for 1 to 1.5 millisecond, for setting the driving mechanism into motion and for accelerating the motor. The duration of each consecutive pulse is either equal or shorter than the former. In some embodiments, the second phase has a minimal pulse period $t_2$ of about 0.5 milliseconds. This trend is turned over when the motor speed is decreased, i.e., in this phase the motor is decelerating and each period $t_3$ of each pulse is either equal or longer than the former.

For example, the duration of the n pulses of an exemplary pulse train can be written as shown in the following equation:

$$t_1 \geq t_2 \geq t_3 \geq \ldots \leq t_{n-1} \leq t_n$$

Since a pulse duration (t) is inversely proportional to the angular velocity of the motor ($\omega$), ($t \propto 1/\omega$), the above equation can be accordingly rewritten as follows:

$$\omega_1 \geq \omega_2 \geq \omega_3 \geq \ldots \leq \omega_{n-1} \leq \omega_n$$

According to some embodiments, every pulse is tailored to rotate the motor's axis through an identical angle (known as a 'step'). Enabling a constant angular rotation resulting from each discrete pulse and providing the same amount of fluid is highly advantageous in that it simplifies the dispensing pump control and calibration, for example, when calculating the number of pulses needed to deliver a required amount of therapeutic fluid. This is achieved by maintaining constant the multiple of pulse duration by the rotational velocity it causes:

$$t_1 \cdot \omega_1 = t_2 \cdot \omega_2 = t_3 \cdot \omega_3 = \ldots t_{n-1} \cdot \omega_{n-1} = t_n \cdot \omega_n = 18°$$

Figure 13:
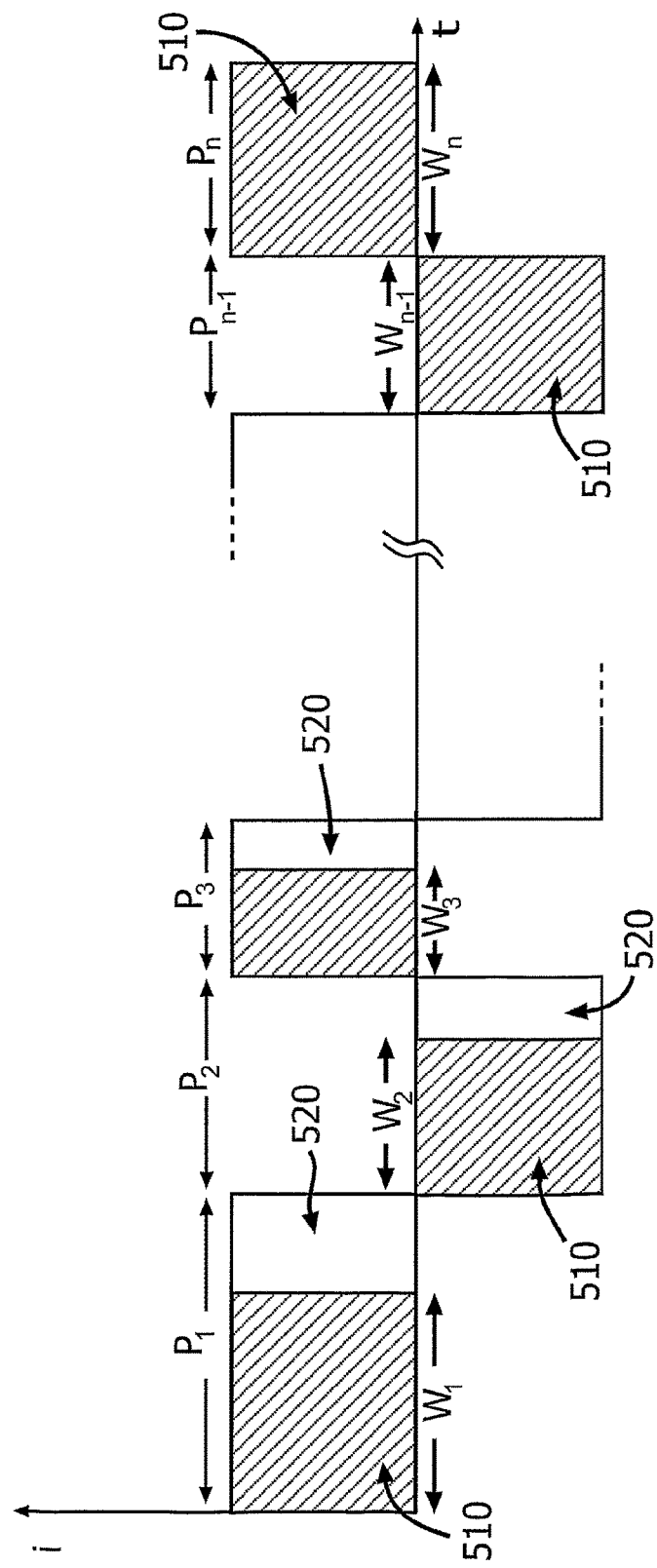
FIG. 13 is a plot illustrating an energy distribution during a pulse train implementing the power profile shown in FIG. 10*b*.
Figure 14:
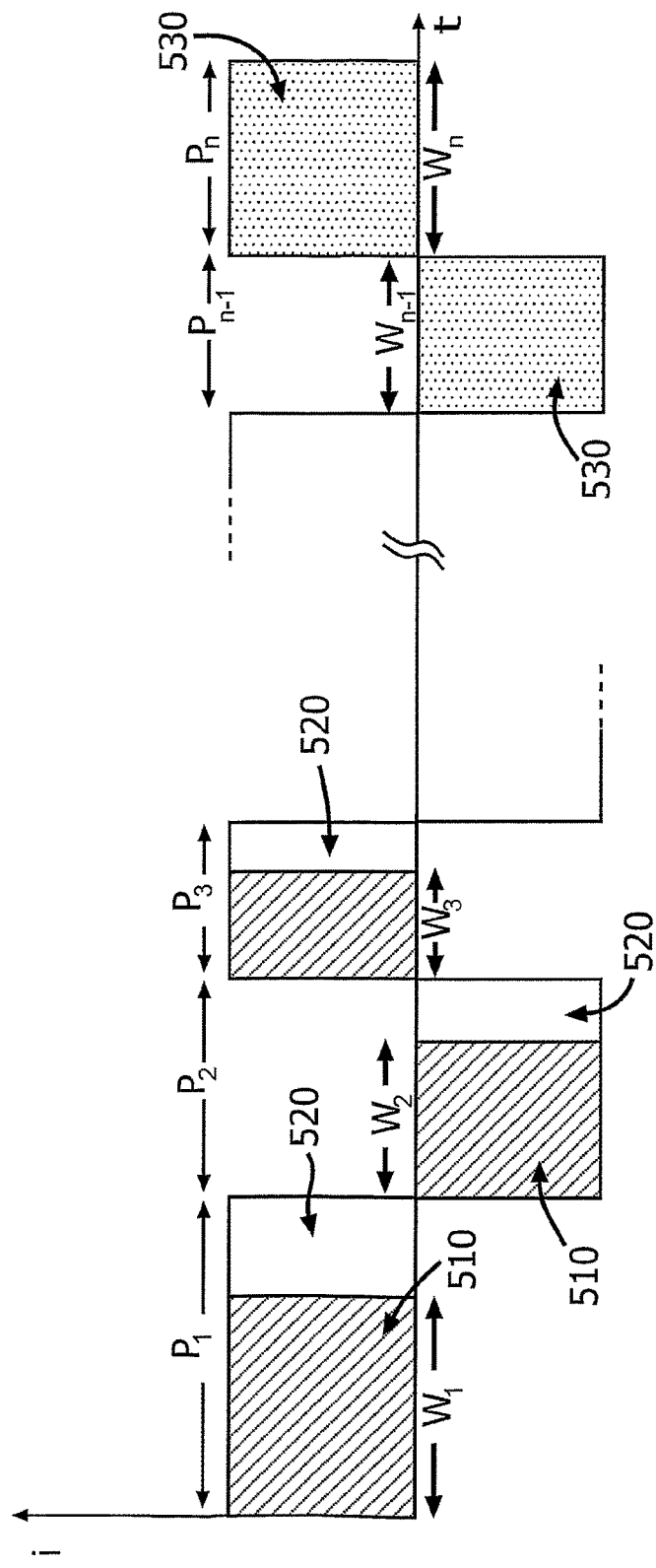
FIG. 14 is a plot illustrating an energy distribution during a pulse train implementing the power profile shown in FIG. 11*b*.

FIGS. 13-14 shows current (i) supplied to the motor versus time (t), according to some embodiments. Conventional methods for supplying energy to motors of infusion devices employ pulses in which a constant level of power is provided to the motor during each pulse period (i.e., a 100% duty cycle). This method can be employed to the device disclosed herein as well, i.e., power pulse trains may be supplied to the motor while each pulse train includes pulses of power during which power would be supplied non-invariantly at three various levels $b_1$, $b_2$ and $b_3$ lasting during respective periods $t_1$, $t_2$ and $t_3$ following without interruption.

In some embodiments, supply of power may be organized during each pulse with interruptions. As shown schematically in FIG. 13 there could be provided three different operational phases and each pulse of the pulse train includes:

A discharge phase (510)—pulsed power is provided to the motor by discharging a capacitor.

A null phase (520)—power supply is interrupted and power is not supplied to and neither generated by the motor.

A charge phase (530)—energy is generated by the motor and this energy can be supplied to power consuming components.

The pulses typically include discharge (510) and null (520) phases or null (520) and charge (530) phases but may include only discharge (510) or charge (530) phases.

FIG. 13 shows a graph of the current (i) supplied to the motor versus time (t), for generating the angular velocity according to principles described in connection with FIGS. 10a-b. The graph shows a single pulse train, which includes three initial pulses. Each one of initial pulses (e.g., the pulses designated as $p_1$, $p_2$ and $p_3$) have two phases: a discharge phase (510) (designated as $w_1$, $w_2$ and $w_3$), followed by a null phase (520).

In some embodiments, the null phase (520) is 10% to 30% of the pulse period, i.e., the width of these pulses is of 70% to 90%. In some embodiments, the dispensing pump controller applies pulse width modulation (PWM) for changing the width of the pulses to generate the determined pulse train. It should be appreciated that other methods for exploiting the motor's inertia for reducing the energy supply may be implemented, such as by changing the pulse period, amplitude, or shape (e.g., triangle, square, sine wave).

Halting motor operation is carried out by the last pulses of the pulse train (e.g., $p_{n-1}$ and $p_n$). The discharge phase (510) of these pulses equals the duty cycle; $p_{n-1}=\omega_{n-1}$ and $p_n=\omega_n$. This causes the motor to stop almost immediately, so that no excess fluid is delivered by the dispensing unit.

FIG. 14 shows a graph of current (i) supplied to the motor versus time (t), for implementing the principle described above in connection with FIGS. 10a-b. The graph shows a pulse train. The last pulses of the pulse train (e.g., $p_{n-1}$ and $p_n$) include a single phase, i.e., the charge phase (530). This mode of operation enables the motor to generate energy due to its rotation and to transfer it to an energy storage device.

The halting method is shown in FIGS. 11a-b and may require the use of a sensing and monitoring device (e.g., a sensor) to detect the relative position (i.e., angle) of the rotary wheel. The sensing and monitoring device may be required to achieve an accurate fluid delivery employing a flow correction mechanism.

Although particular embodiments have been disclosed herein in detail, this has been done by way of example for purposes of illustration only, and is not intended to be limiting with respect to the scope of the claims. In particular, it is contemplated by the inventors that various substitutions, alterations, and modifications may be made without departing from the spirit and scope of the devices and methods defined by the claims. Other aspects, advantages, and modifications are considered to be within the scope of the claims. The claims presented are representative of the devices and methods disclosed herein. Other, presently unclaimed devices and methods, are also contemplated. The inventors reserve the right to pursue such devices and methods in later claims.

The following examples serve to illustrate embodiments of the disclosed devices and methods and are given for illustrative purposes only and are not intended to limit the present disclosure.

EXAMPLES

Figure 15:
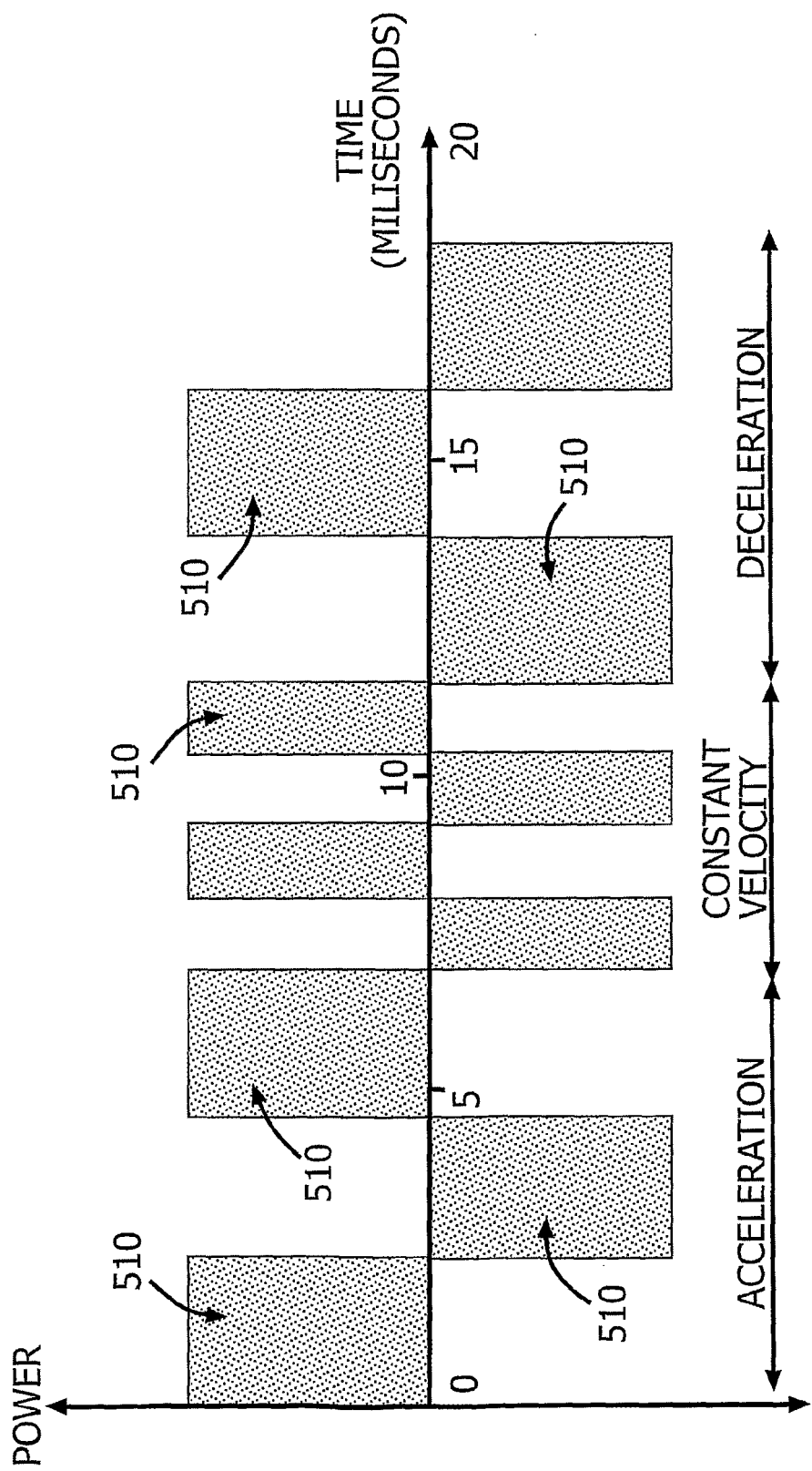
FIG. 15 is a plot illustrating an example of a pulse train implementing the rotational velocity shown in FIG. 10*a*.
Figure 16:
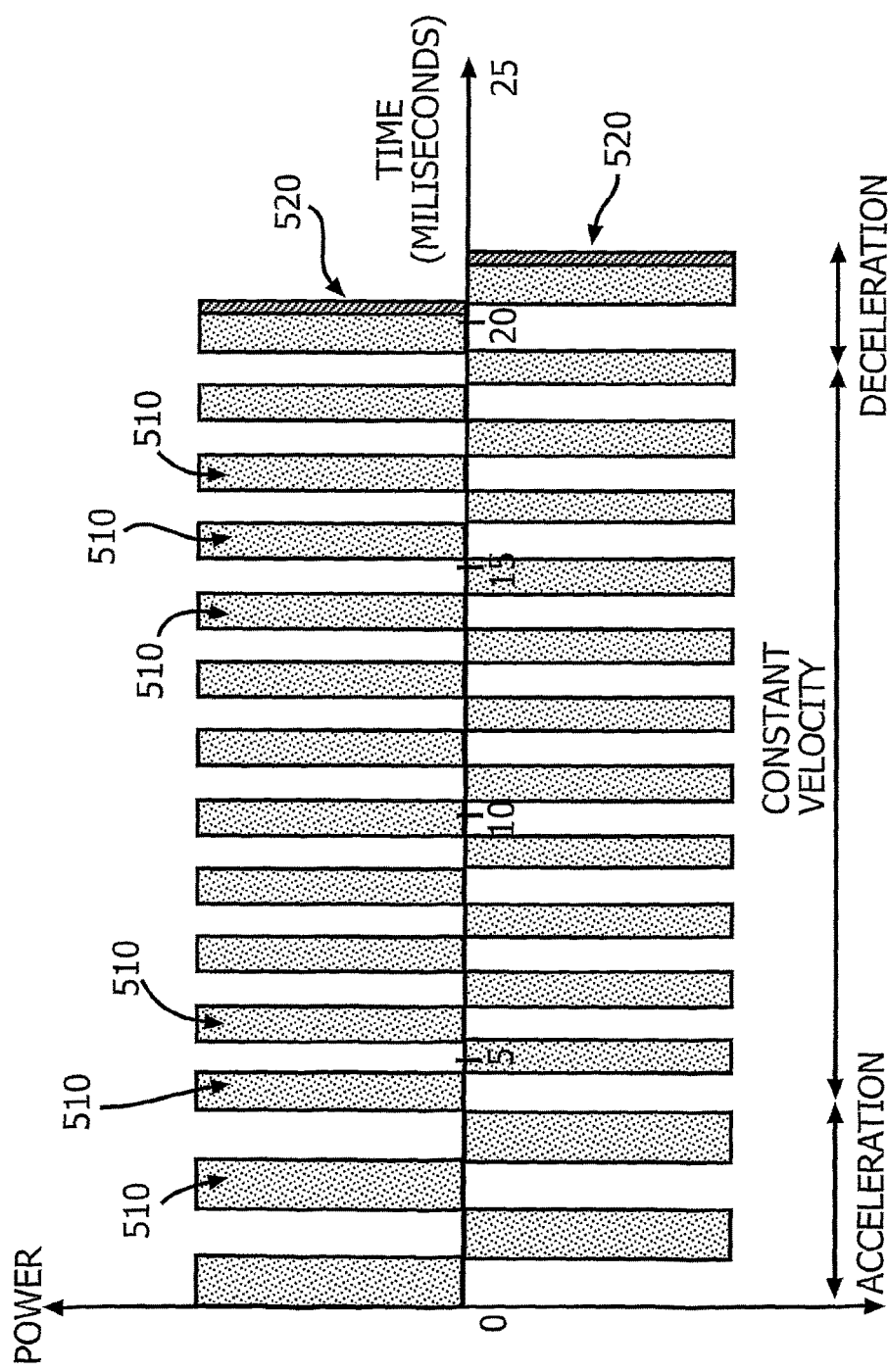
FIG. 16 is a plot illustrating an example of a pulse train implementing the rotational velocity shown in FIG. 10*a*.

FIGS. 15, 16 and 17 show examples of pulse train supplied to the motor according to some embodiments. These figures show the discharge phase (510), in which power is supplied to the motor, the null phase (520) in which no power is supplied to the motor and the charge phase (530) when power is generated by the motor.

The pulse trains were tailored to reduce the power provided to the motor while each pulse rotates the motor by 20 degrees. The power source in these examples is a zinc-air button battery, a 0.2 F capacitor and two phase motor commercially provided by Nidec Copal Corporation (U.S.A.).

The pulses are provided by PWM and/or by changing the pulse period.

Example 1

FIG. 15 shows a pulse train for rotating the motor by 160 degrees composed of three sets of pulses:
The first set of pulses is applied for accelerating the motor and includes three pulses lasting for 2.3 milliseconds.
The second set of pulses is designed for maintaining the motor speed and includes four pulses, each having a 1.15 millisecond period. This set of pulses rotates the motor by the same angle as the first set but requires 50% less power. To increase the energy efficiency, the last two pulses may have 80% width of the duty cycle.
The third set of pulses is for stopping the motor and is identical to the first set but in reversed phase.
In this example all the pulses have 100% pulse width (i.e., the pulse width equals the pulse duration).

Example 2

FIG. 16 shows a pulse train designed to rotate the motor by 520 degrees at a lower rotation velocity than that disclosed in Example 1. This pulse train is composed of three sets of pulses:
The first set of pulses is applied for accelerating the motor and includes four pulses lasting for 1.0 millisecond.
The second set of pulses is designed for maintaining the motor speed and includes 22 pulses, each having a 0.7 millisecond period. If the pulses in this set were tailored as the first set (as described in the prior art), the energy consumption of this set would be 40% higher.
The third set of pulses includes two stop pulses lasting for 1.0 millisecond, wherein a 90% duty cycle is applied to stop the motor rotation.

Example 3

FIG. 17 shows a pulse train that does not apply power to stop the motor. The pulse train includes two sets of pulses:
The first set of pulses is applied for accelerating the motor and includes four pulses lasting for 1.0 millisecond.
The second set of pulses is designed for maintaining the motor speed and includes 22 pulses, each having a 0.7 millisecond period.
Also shown are two pulses (530) supplied by the motor for recharging the capacitor, i.e., the motor functions as a dynamo by transferring kinetic energy to electrical power.

Example 3 requires less energy than the pulse train described in Example 2 and provides two more steps to the motor (which are applied to stop the motor in Example 2). The inertia of the motor at the end of this pulse train can be converted by the motor to electrical power, which can be provided to other electrical components of the dispensing unit. This pulse train requires 29.1 J, provides 26 steps of rotation and can also retrieve part of the excess power provided to the motor. A standard method of motor activation would be composed of 20 pulses lasting 1.0 millisecond each, whereby at least two of them are applied for stopping the motor. Thus, less than 20 steps can be provided in this method.

What is claimed is:

1. A medical device for delivering fluid to a body or sensing body analyte, the medical device comprising:
a pumping mechanism;
a driving mechanism for activating said pumping mechanism to dispense fluid; and
a power source housed in the medical device and electrically coupled to said driving mechanism and having an energy storage device for providing a pulsed power to activate said driving mechanism, wherein the pulsed power operates periodically between an accumulation mode in which the power source charges the energy storage device and a release mode in which the energy storage device delivers the pulsed power; and
a DC-DC converter to increase voltage of the pulsed power delivered in the release mode to the driving mechanism by the energy storage device.

2. The medical device according to claim 1, wherein the pulsed power is transferred to said driving mechanism using at least one pulse train pattern.

3. The medical device according to claim 2, wherein during said activation of said driving mechanism at least two different pulses are transferred to said driving mechanism.

4. The medical device according to claim 3, wherein said at least two different pulses are characterized by a width, a frequency, a duty cycle, a period and/or energy delivered by each pulse.

5. The medical device according to claim 3, wherein a controller is coupled to a sensing and monitoring device to adjust a speed of the driving mechanism and measure the speed of the driving mechanism.

6. The medical device according to claim 4, wherein at least one pulsed of said at least two different pulses comprises a first period of time during which energy is delivered and a second period of time during which energy is not delivered.

7. The medical device according to claim 2, wherein said at least one pulse train pattern is configured to achieve one or more of the following:
maintaining a constant rotational velocity of said driving mechanism;
altering a rotational acceleration of said driving mechanism; or
altering a rotational velocity of said driving mechanism.

8. The medical device according to claim 2, wherein said driving mechanism is stopped using at least one pulse of at least one pulse train pattern.

9. The medical device according to claim 1, wherein said medical device further comprises a controller for adjusting the at least one pulse train pattern.

10. The medical device according to claim 9, wherein adjusting the at least one pulse train pattern is based on the energy stored in the energy storage device.

11. The medical device according to claim 1, wherein the pulse power from the energy storage device causes rotational velocity of the driving mechanism to: increase during a first period of time due to a first amount of constant energy delivered, remain constant during a second period of time due to a second amount of constant energy delivered, and decrease during a third period of time due to a third amount of constant energy delivered.

12. The medical device according to claim 1, wherein the power source is a zinc-air battery.

13. The medical device according to claim 1, comprising:
a reusable part containing at least part of said driving mechanism and electronic components, including an energy storage component; and
a disposable part having a reservoir, wherein the power source is electrically coupled to at least one of said electronic components for supplying energy upon connection of said reusable part and said disposable part.

14. The medical device according to claim 1, further comprising:
a skin adherable cradle unit;
a remote control unit; and
a dispensing unit having the pumping mechanism and the driving mechanism and being connectable to and disconnectable from the cradle unit, wherein said remote control unit communicates with the dispensing unit for its operation.

15. The medical device according to claim 1, wherein the fluid comprises insulin.

16. A method of for delivering fluid to a body or sensing body analyte which comprises utilizing the medical device of claim 1.

* * * * *